(12) United States Patent
Shuler et al.

(10) Patent No.: US 8,748,180 B2
(45) Date of Patent: Jun. 10, 2014

(54) MICROFLUIDIC DEVICE FOR PHARMACOKINETIC-PHARMACODYNAMIC STUDY OF DRUGS AND USES THEREOF

(75) Inventors: Michael L. Shuler, Ithaca, NY (US); Jong Hwan Sung, Seoul (KR)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/387,585

(22) PCT Filed: Jul. 29, 2010

(86) PCT No.: PCT/US2010/043743
§ 371 (c)(1), (2), (4) Date: Feb. 17, 2012

(87) PCT Pub. No.: WO2011/014674
PCT Pub. Date: Feb. 3, 2011

(65) Prior Publication Data
US 2012/0135452 A1 May 31, 2012

Related U.S. Application Data

(60) Provisional application No. 61/229,575, filed on Jul. 29, 2009.

(51) Int. Cl.
*C12N 5/00* (2006.01)
*C12Q 1/02* (2006.01)
*A01N 1/02* (2006.01)
*C12M 1/00* (2006.01)

(52) U.S. Cl.
USPC ............. 435/382; 435/29; 435/395; 435/383; 435/284.1; 435/289.1

(58) Field of Classification Search
USPC ............. 435/29, 382, 395, 284.1, 289.1, 383
See application file for complete search history.

(56) References Cited

U.S. PATENT DOCUMENTS

| | | | |
|---|---|---|---|
| 7,288,405 B2 | 10/2007 | Shuler et al. | |
| 7,314,718 B1 | 1/2008 | Dasgupta et al. | |
| 2002/0173033 A1 | 11/2002 | Hammerick et al. | |
| 2003/0175824 A1 | 9/2003 | Pishko et al. | |
| 2004/0132166 A1 | 7/2004 | Miller et al. | |
| 2005/0266393 A1 | 12/2005 | Baxter et al. | |
| 2007/0015275 A1 | 1/2007 | Shuler et al. | |
| 2007/0275435 A1 | 11/2007 | Kim et al. | |
| 2008/0233607 A1 | 9/2008 | Yu et al. | |
| 2009/0074623 A1 | 3/2009 | Park et al. | |
| 2011/0183312 A1* | 7/2011 | Huang | 435/3 |

FOREIGN PATENT DOCUMENTS

WO WO-2008040015 A2 4/2008

OTHER PUBLICATIONS

Ma et al. Characterization of Drug Metabolites and Cytotoxicity Assay Simultaneously Using an Integrated Microfluidic Device; Lab on a Chip, vol. 9 (Nov. 19, 2008) pp. 232-238.*
International Search Report for International Application No. PCT/US10/43743 mailed Apr. 29, 2011 (3 pgs.).
International Preliminary Report on Patentability (Chapter I of the PCT) for International Application No. PCT/US10/43743 mailed Feb. 9, 2012 (6 pgs.).

* cited by examiner

*Primary Examiner* — Susan Hanley
*Assistant Examiner* — Paul Martin
(74) *Attorney, Agent, or Firm* — Harris Beach PLLC

(57) ABSTRACT

A microfluidic device for culturing cells, termed a microscale cell culture analog (μCCA), is provided. The microfluidic device allows multiple cell or tissue types to be cultured in a physiologically relevant environment, facilitates high-throughput operation and can be used for drug discovery. The microfluidic device uses gravity-induced fluidic flow, eliminating the need for a pump and preventing formation of air bubbles. Reciprocating motion between a pair of connected reservoirs is used to effect the gravity-induced flow in microfluidic channels. Bacterial contamination is reduced and high throughput enabled by eliminating a pump. The microfluidic device integrates a pharmacokinetic-pharmacodynamic (PK-PD) model to enable PK-PD analyses on-chip. This combined in vitro/in silico system enables prediction of drug toxicity in a more realistic manner than conventional in vitro systems.

31 Claims, 10 Drawing Sheets

Figure 1D:
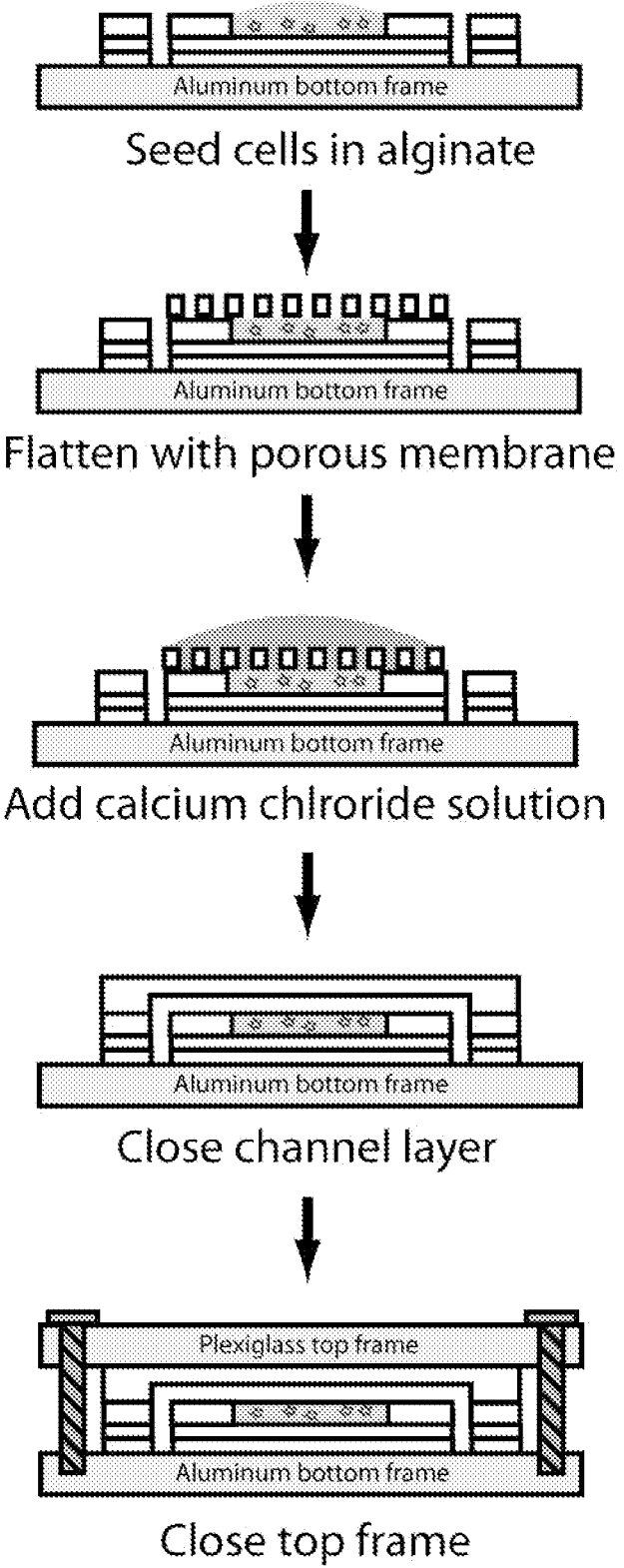

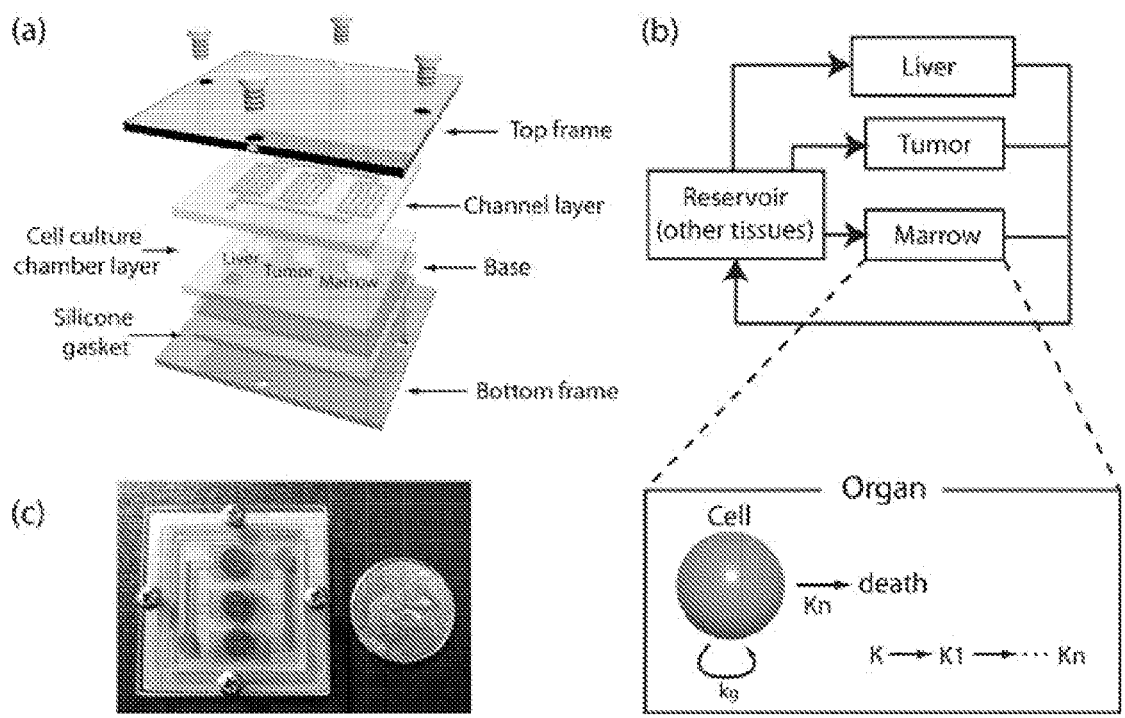
FIGS. 1a-c

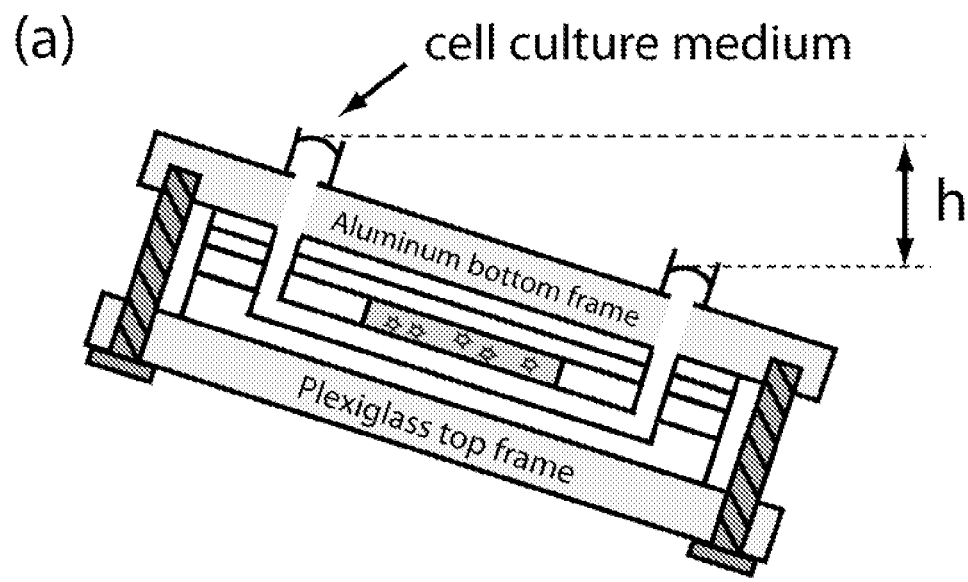
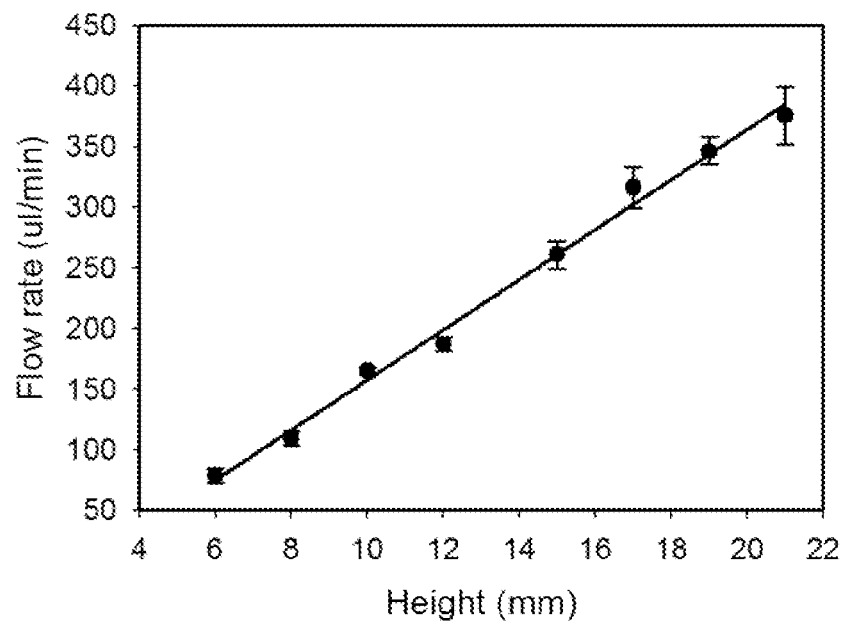
FIGS. 2a-b

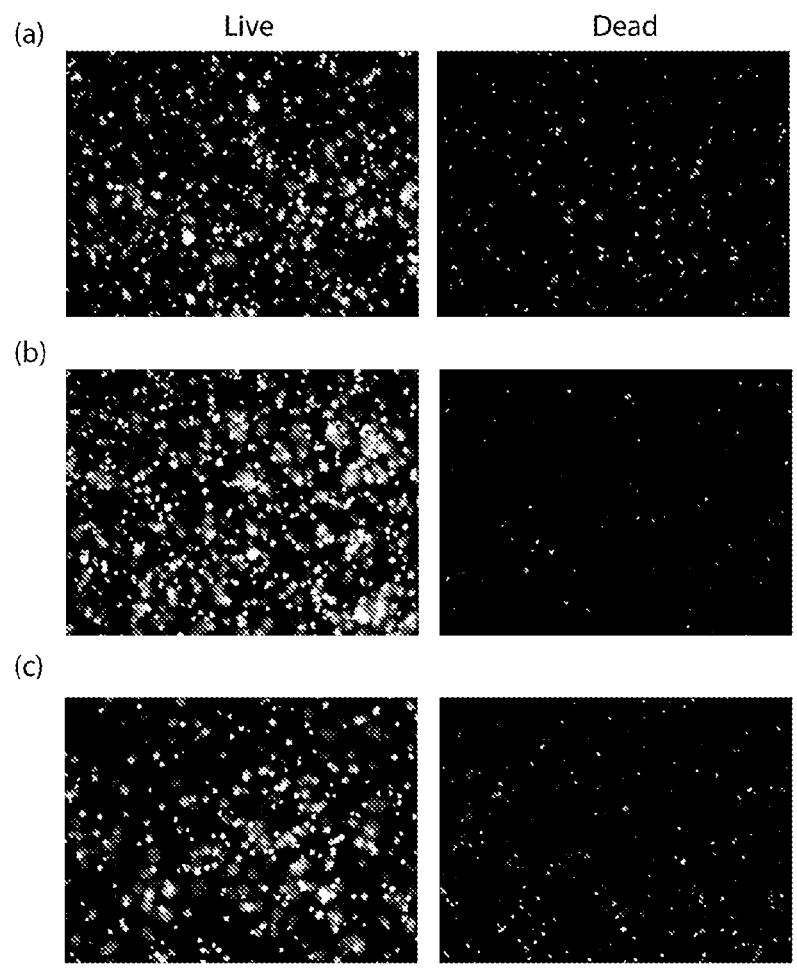
FIGS. 6a-c

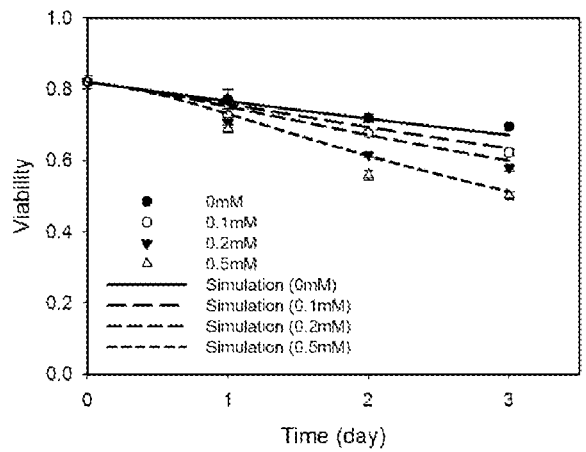
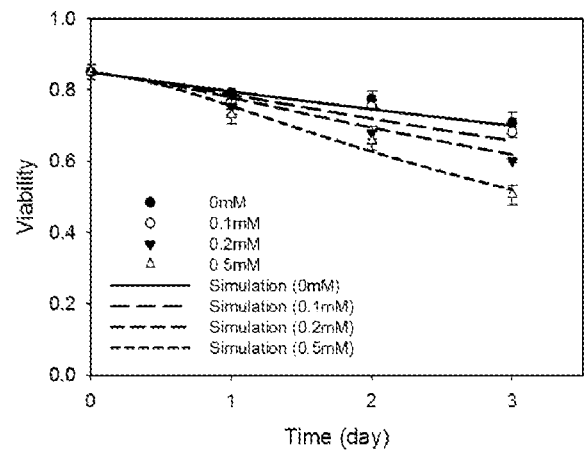
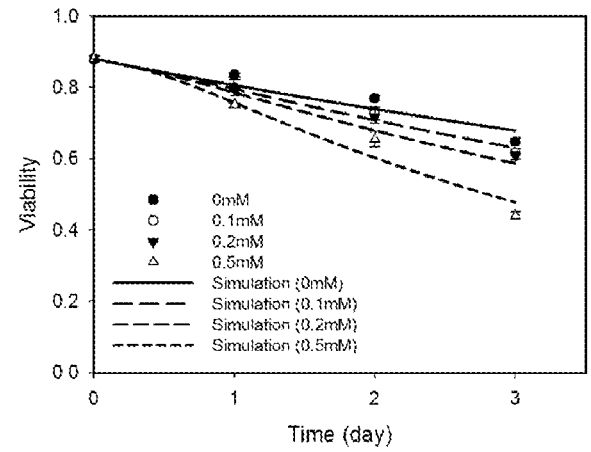
FIGS. 7a-c

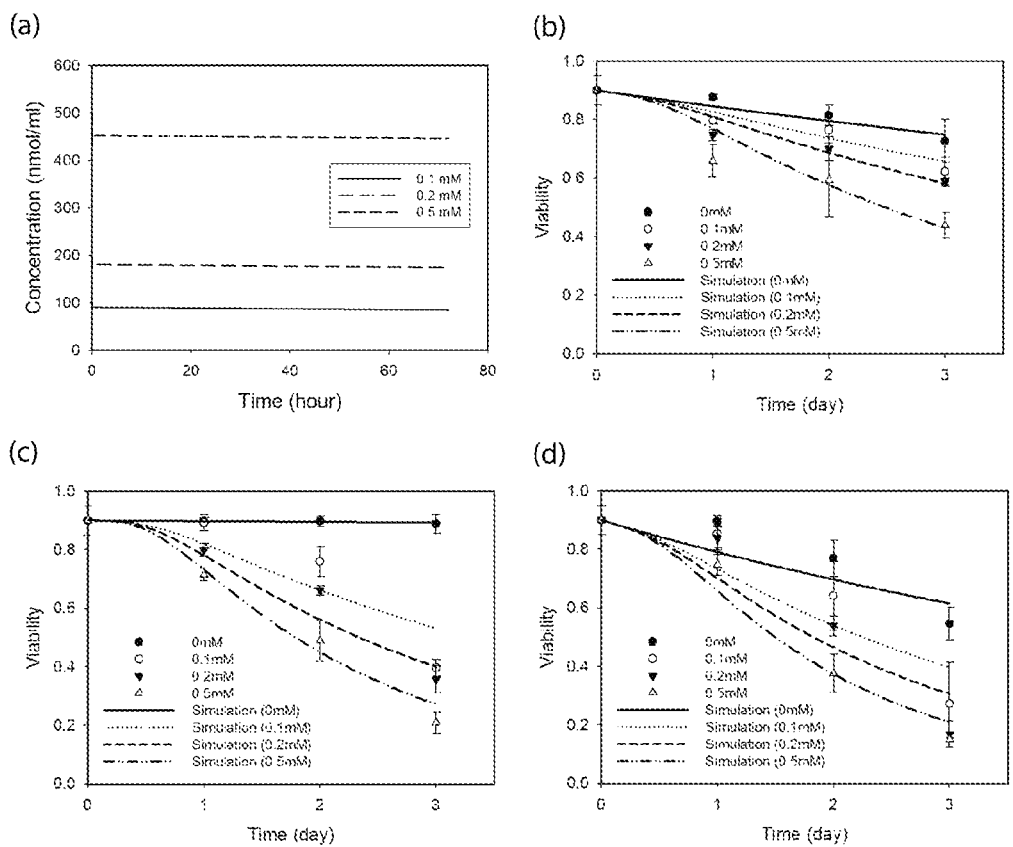
FIGS. 8a-d

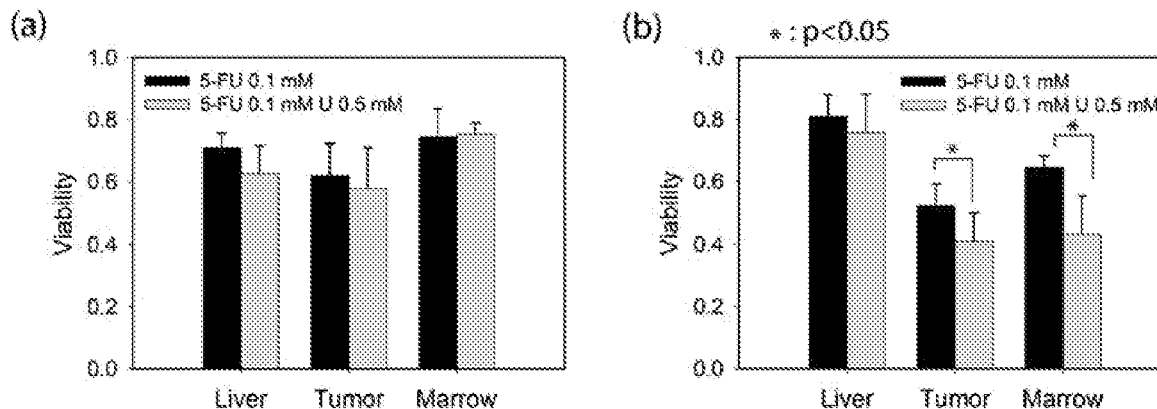
FIGS. 9a-b
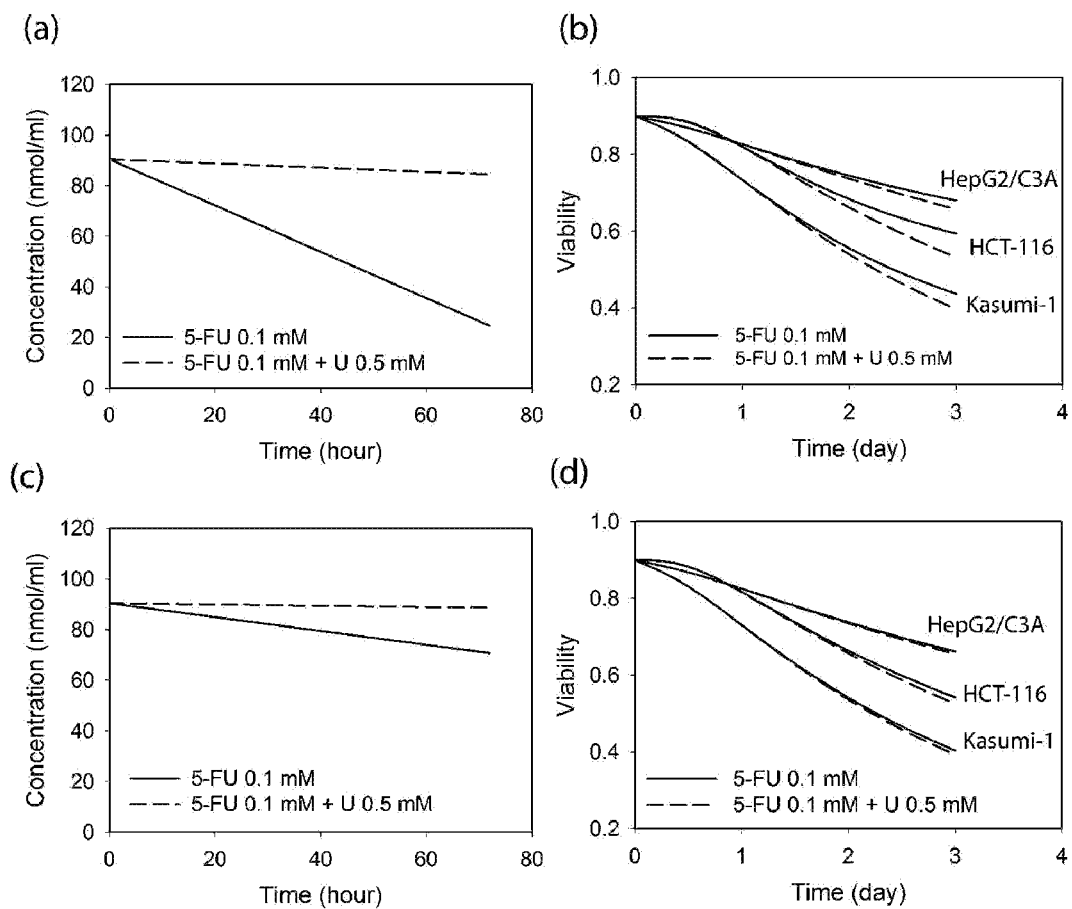
FIGS. 10a-d

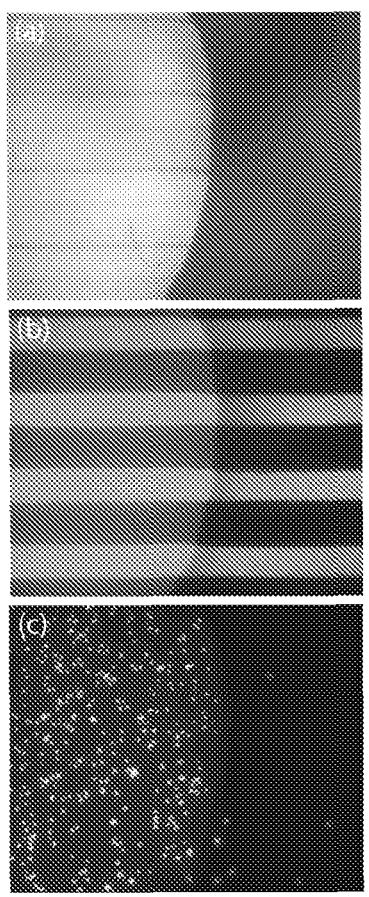
FIGS. 11a-c

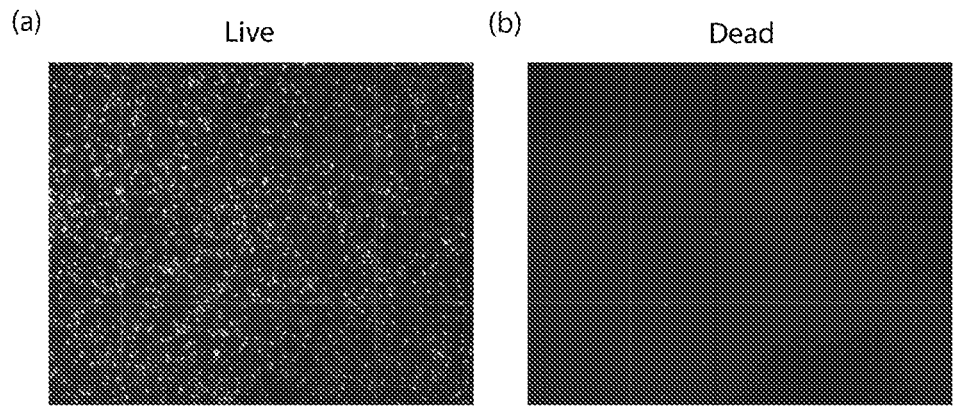
FIGS. 12a-b
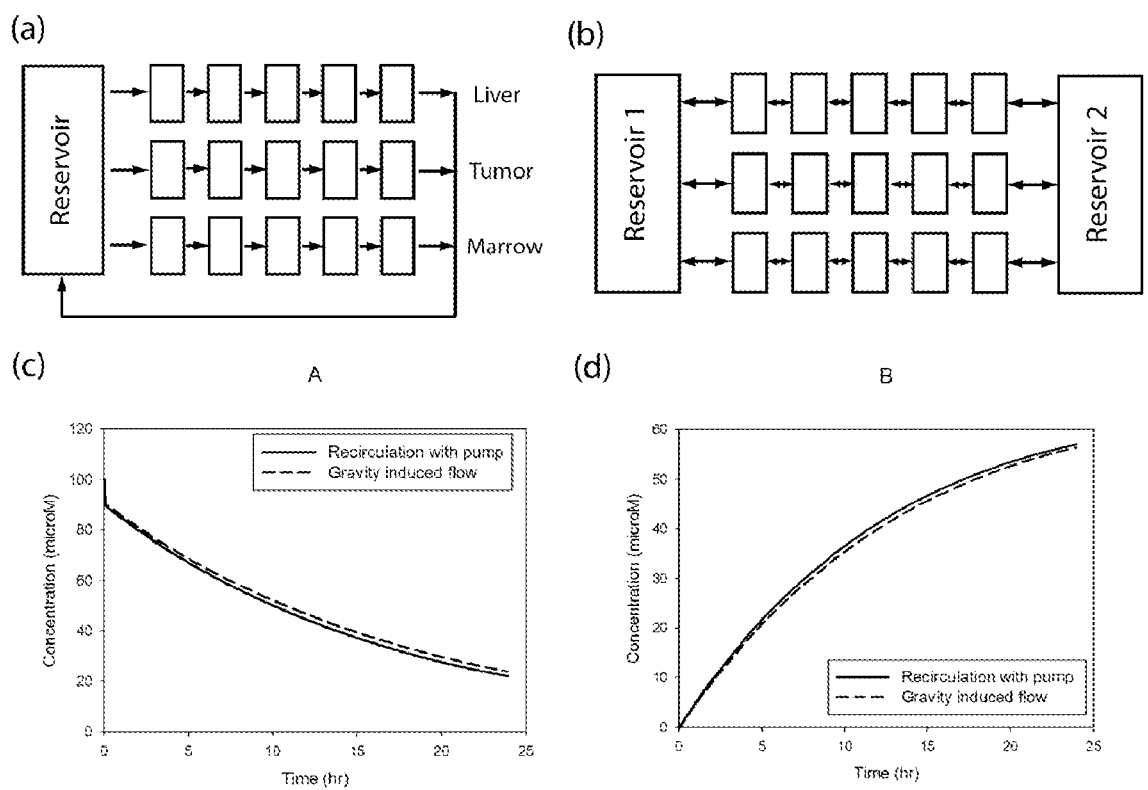
FIGS. 13a-d

MICROFLUIDIC DEVICE FOR PHARMACOKINETIC-PHARMACODYNAMIC STUDY OF DRUGS AND USES THEREOF

CROSS-REFERENCE TO RELATED APPLICATIONS

This application is a national stage application under 35 U.S.C. §371 of PCT Application No. PCT/US2010/043743, filed Jul. 29, 2010, entitled Microfluidic Device for Pharmacokinetic-Pharmacodynamic Study of Drugs and Uses Thereof, which claims priority to and the benefit of U.S. provisional patent application Ser. No. 61/229,575, entitled Microfluidic Device For Pharmacokinetic-Pharmacodynamic Study of Drugs and Uses Thereof, filed Jul. 29, 2009, which is incorporated herein by reference in its entirety.

STATEMENT REGARDING FEDERALLY SPONSORED RESEARCH OR DEVELOPMENT

This invention was made with Government support under Grant Number W9132T-07 from the Army Corp of Engineers (CERL). The United States Government has certain rights in the invention.

1. TECHNICAL FIELD

The present invention relates to microfluidic devices for in vitro cell-based assays. The invention also relates to microfluidic devices for use in pharmacokinetic and/or pharmacodynamic studies of drugs. The invention further relates to methods for in vitro culturing of cells. The invention also relates to methods for pharmacokinetic and/or pharmacodynamic characterization of drugs. The invention also relates to methods for performing cell-based assays in microfluidic devices. The invention also relates to high-throughput screening methods.

2. BACKGROUND OF THE INVENTION

One of the fundamental challenges during the drug development process is extrapolation of the results of in vitro cell-based assays to human responses. The most common form of in vitro cell-based assay is the multiwell plate assay. These assays, however, often give results that are different from in vivo responses, which increase the probability of the drug failing in trials. The main reasons for inaccurate predictions by such multiwell plate assays are that (1) only single cells types are generally tested in a single well, which does not provide complex multi-organ interactions in the human body, and that (2) cells are cultured in 2-D monolayer cell culture inside the wells, and the behavior of cells cultured in 2-D monolayer is vastly different from the behavior of cells in their native tissue, where they are surrounded by various extracellular matrix and neighboring cells.

Microfluidics has been introduced as a way of increasing the efficiency of cell-based tests. Although current microfluidic devices can increase the efficiency of high-throughput screening by automated fluid introduction through microfluidic channels and valves, it is essentially the same concept as the multiwell plate-based assay system; a single cell type is tested in a physiologically non-relevant environment. These current microfluidic devices share the same limitations as multiwell plate systems.

Approximately only one in ten drugs entering clinical trials finally becomes approved during the drug development (I. Kola and J. Landis, Nat. Rev. Drug Discovery, 2004, 3, 711-715). One of the main causes for such a high attrition rate is unforeseen lack of efficacy or toxicity which is not revealed until the later stages of clinical trials. Given the fact that the majority of drug development cost occurs in the later phases of the process (M. Dickson and J. P. Gagnon, Nat. Rev. Drug Discovery, 2004, 3, 417-429), the ability to predict the toxicity of drugs earlier will save a significant amount of resources. The high attrition rate of drug candidates in animal and human trials indicates that the current in vitro systems for studying drug toxicity need to be improved. One major shortcoming of conventional multi-well plate assays is that they lack multi-organ interactions, and therefore cannot reproduce the pharmacokinetics (PK) of drugs, which plays a significant role in determining the pharmacological effect of drugs (J. H. Lin and A. Y. Lu, Pharmacol. Rev., 1997, 49, 403-449).

The potential importance of microfluidic systems in improving the drug development process has been widely recognized (L. Kang, B. G. Chung, R. Langer and A. Khademhosseini, Drug Discovery Today, 2008, 13, 1-13). Microfluidic systems with perfusion cell culture offer a great potential for drug screening in a high-throughput manner (M. S. Kim, W. Lee, Y. C. Kim and J. K. Park, Biotechnol. Bioeng., 2008, 101, 1005-1013; M. S. Kim, J. H. Yeon and J. K. Park, Biomed. Microdevices, 2007, 9, 25-34; M. Y. Lee, R. A. Kumar, S. M. Sukumaran, M. G. Hogg, D. S. Clark and J. S. Dordick, Proc. Natl. Acad. Sci. U.S.A., 2008, 105, 59-63; Z. Wang, M. C. Kim, M. Marquez and T. Thorsen, Lab Chip, 2007, 7, 740-745). Microfluidics can be especially useful for reproducing the PK of drugs, since structures with multiple components such as a metabolizing component (for example, liver) and a target component (for example, tumor) can be connected with fluidic channels for multi-organ interactions. For example, Ma et al. developed a three-layer microfluidic system to test metabolism dependent toxicity of drugs, consisting of a top-layer for feeding drugs, a middle layer with human liver microsomes, and a bottom-layer for cell culture chambers (B. Ma, G. Zhang, J. Qin and B. Lin, Lab Chip, 2009, 9, 232-238). In another study, a hepatocyte-bioreactor was developed to assess hepato-activated transformation of substrates (H. G. Koebe, C. J. Deglmann, R. Metzger, S. Hoerrlein and F. W. Schildberg, Toxicology, 2000, 154, 31-44). These systems successfully demonstrated in vitro observation of metabolism-dependent drug toxicity. However, they are still far from the faithful reproduction of in vivo situations, since they do not capture the true dynamics of drug exposure to the human body.

Although microfluidic systems have a great potential in enhancing the drug development process, actual applications of microfluidic systems in medical or life science area have been limited. One reason for this is because current microfluidic devices require specialized skills for fabrication and operation, which makes it difficult to be used by non-experts (I. Meyvantsson, J. W. Warrick, S. Hayes, A. Skoien and D. J. Beebe, Lab Chip, 2008, 8, 717-724). In addition, microfluidic cell cultures have several issues that need more in depth study, such as biocompatibility of materials, maintenance of sterility, formation of air bubbles, and the effect of shear stress on cells (L. Kim, Y. C. Toh, J. Voldman and H. Yu, Lab Chip, 2007, 7, 681-694). There has been a substantial amount of progress in terms of developing highly complex microfluidic devices for high throughput implementation (S. T. Yang, X Zhang and Y. Wen, Curr. Opin. Drug Discovery Dev., 2008, 11, 111-127), but not much progress has been achieved in terms of simplifying the design and improving the usability of microfluidic systems.

There is therefore a need in the art for an improved microfluidic system that can be used as an in vitro system for studying drug toxicity. There is also a need in the art for a microfluidic system that simulates multi-organ interactions and reproduces the pharmacokinetics (PK) and/or pharmacodynamics (PD) of drugs.

Citation or identification of any reference in Section 2, or in any other section of this application, shall not be considered an admission that such reference is available as prior art to the present invention.

3. SUMMARY OF THE INVENTION

A microfluidic device for culturing cells is provided comprising:
- a base layer;
- a cell culture chamber layer comprising one or more cell culture chambers; and
- a fluidic channel layer comprising a plurality of fluid channels;

wherein:
- the cell culture chamber layer is positioned between the fluidic channel layer and the base layer so that the one or more cell culture chambers are fluidically connected to one or more fluid channels of the plurality; and
- the fluid channels have defined geometries that produce one or more desired flow rates through the fluid channels that simulate one or more physiological environments or conditions of interest. In one embodiment, the flow rate into a one cell culture chamber in the cell culture chamber layer can differ from the flow rate into another cell culture chamber on the cell culture chamber layer.

In one embodiment, the microfluidic device is used for conducting a pharmacokinetic, a pharmacodynamic or a pharmacokinetic-pharmacodynamic (PK-PD) analysis of an effect of an agent (e.g., drug, chemical composition, toxin) of interest on the cultured cells.

In another embodiment, the physiological environment or condition of interest is blood flow distribution to an organ or tissue of interest.

In another embodiment, the physiological environment or condition of interest is toxicity of an agent of interest, or metabolism of an agent of interest, wherein the metabolism renders the agent of interest toxic or nontoxic (i.e., detoxifies the agent).

In another embodiment, the microfluidic device comprises a bottom frame.

In another embodiment, the bottom frame comprises a pair of reservoirs.

In another embodiment, the bottom frame comprises aluminum.

In another embodiment, the microfluidic device comprises a top frame

In another embodiment, the top frame comprises a plastic.

In another embodiment, the microfluidic device comprises a gasket.

In another embodiment, the gasket is silicone.

In another embodiment, the cell culture chamber layer or the fluidic channel layer comprises PDMS.

In another embodiment, the microfluidic device comprises a bottom frame, a gasket and a top frame.

In another embodiment, the base layer, the cell culture chamber layer and the fluidic channel layer are fastened with fasteners.

In another embodiment, the bottom frame, the gasket, the base layer, the cell culture chamber layer, the fluidic channel layer and the top frame are fastened with fasteners.

In another embodiment, the bottom frame has an inlet hole and an outlet hole, the base layer has an inlet hole and an outlet hole, and the cell culture chamber layer has an inlet hole and an outlet hole, wherein the inlet holes of the bottom frame, the base layer and the cell culture chamber layer and the outlet holes of the bottom frame, the base layer and the cell culture chamber layer align with one another, thereby allowing flow of fluid through the cell culture chamber layer and the fluidic channel layer.

In another embodiment, the cultured cells are derived from one or more unicellular or multicellular organisms.

In another embodiment, the cultured cells comprise a single cell type.

In another embodiment, the cultured cells comprise a plurality of cell types.

In another embodiment, a single cell type of the plurality is cultured in a single cell culture chamber.

In another embodiment, two or more cell types of the plurality are cultured in a single cell culture chamber.

In another embodiment, the cultured cells form a tissue.

In another embodiment, the cultured cells are cultured (or grown) in or on a 2-D matrix, a 3-D matrix or a scaffold.

In another embodiment, the cultured cells are encapsulated.

In another embodiment, cultured cells are grown in one or more fluid channels of the plurality of fluid channels.

In another embodiment, the cultured cells are endothelial cells.

In another embodiment, a fluid flow pattern is induced by gravity, static flow (passive diffusion) or pump perfusion.

In another embodiment, the gravity induced fluid flow pattern is induced by reciprocating motion.

In another embodiment, the microfluidic device comprises one or more pairs of reservoirs, wherein the reciprocating fluid motion is between the pair of reservoirs.

In another embodiment, the pair of reservoirs is positioned on the bottom frame.

In another embodiment, the gravity induced fluid flow pattern simulates blood circulation through a tissue or organ of interest.

In another embodiment, the components of the microfluidic device are autoclavable or sterilizable.

In another embodiment, the microfluidic device can be reversibly assembled and disassembled.

In another embodiment, the assembly or disassembly is conducted in a sterile manner, e.g., by art-known methods for sterile assembly or disassembly.

A method for culturing cells or tissues is also provided. The method can comprise the steps of:
- providing the microfluidic device of the invention;
- placing the cells or tissues to be cultured in the microfluidic device; and
- culturing the cells or tissues, wherein the culturing step comprises flowing cell or tissue culture medium through the microfluidic device.

In one embodiment, the method comprises the step of encapsulating cells to be cultured in a hydrogel.

In another embodiment, the cells or tissues are cultured in or on a 2-D matrix, a 3-D matrix or a scaffold.

In another embodiment, the step of flowing cell or tissue culture medium is induced by gravity, static flow (passive diffusion) or pump perfusion.

In another embodiment, the cultured cells comprise multiple cell types or the cultured cells are comprised in a tissue.

In another embodiment, the method comprises the step of performing an analysis or assay of an effect of an agent of interest on the cultured cells or tissue, thereby determining an in vitro effect of the agent of interest on the cultured cells or tissue.

In another embodiment, the in vitro value of the effect is comparable to the in vivo value of the effect for a cell or tissue type of interest.

In another embodiment, the in vitro value is 0.01 to 0.1×, 0.1× to 1×, 1×-10×, 10×-100×, 100×-1000× or greater than 1000× the in vivo value.

In another embodiment, the method comprises the step of performing a pharmacokinetic, a pharmacodynamic or a pharmacokinetic-pharmacodynamic (PK-PD) assay or analysis of an effect of an agent of interest on the cultured cells or tissue, thereby determining an in vitro pharmacokinetic and/or pharmacodynamic effect of the agent of interest on the cultured cells or tissue.

In another embodiment, the in vitro pharmacokinetic or pharmacodynamic value is comparable to the in vivo pharmacokinetic or pharmacodynamic value for a cell or tissue type of interest.

In another embodiment, the in vitro pharmacokinetic or pharmacodynamic value is 0.01 to 0.1×, 0.1× to 1×, 1×-10×, 10×-100×, 100×-1000× or greater than 1000× the in vivo pharmacokinetic or pharmacodynamic value.

In another embodiment, a plurality of microfluidic devices are provided, further comprising the step of conducting a high throughput analysis.

In another embodiment, a plurality of cell types are cultured, and the method further comprises the step of testing the effect of an agent of interest on the plurality of cell types.

In another embodiment, the effect of an agent of interest and its metabolite(s) are tested simultaneously.

A method for performing a pharmacokinetic, a pharmacodynamic or a pharmacokinetic-pharmacodynamic (PK-PD) assay or analysis of an effect of an agent of interest on cultured cells or tissues is also provided. The method can comprise the steps of:

providing the microfluidic device of the invention;
culturing cells or tissues of interest in the microfluidic device;
exposing the cultured cells or tissues to the agent of interest (e.g., a chemical compound, drug, toxin, growth factor, hormone, etc.); and
determining an in vitro pharmacokinetic and/or pharmacodynamic effect of the agent of interest on the cultured cells or tissue.

A method for culturing cells for tissue engineering is also provided. The method can comprise the steps of:

providing the microfluidic device of the invention;
placing the cells to be cultured in the microfluidic device; and
culturing the cells, wherein the culturing step comprises flowing cell culture medium through the microfluidic device; and
harvesting the cultured cells.

In one embodiment, the method comprises the step of encapsulating cells to be cultured in a hydrogel.

In another embodiment, the cells or tissues are cultured in or on a 2-D matrix, a 3-D matrix or a scaffold.

In another embodiment, the step of flowing cell culture medium is induced by gravity, static flow (passive diffusion) or pump perfusion.

In another embodiment, the cultured cells comprise multiple cell types.

A method for assembling a microfluidic device is also provided. The method can comprise the steps of:

providing a bottom frame, a gasket, a base layer, a cell culture chamber layer, a fluidic channel layer and a top frame;
placing the gasket on top of the bottom frame;
placing the base layer on top of the gasket;
placing the cell culture chamber layer on top of the base layer;
placing the fluidic channel layer on top of the cell culture chamber layer with the channels facing down; and
placing the top frame on top of the fluidic channel layer.

In one embodiment, the method can further comprise the step of closing or sealing the microfluidic device.

In another embodiment, the method can further comprise the step of fastening the bottom frame, the gasket, the base layer, the cell culture chamber layer, the fluidic channel layer and the top frame with fasteners.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIGS. 1a-d. (a) A schematic of the microfluidic device and its components. A fluidic channel layer and a cell culture chamber layer are sandwiched together and sealed by top and bottom frames. A silicone gasket and a polycarbonate base can be inserted to promote sealing. (b) An example of a corresponding physiologically based pharmacokinetic (PBPK) model, with liver, tumor and marrow compartment. Below is a pharmacodynamic (PD) model for cell death in each compartment. Although not drawn explicitly, a PD model for each compartment exists separately, and the 'organ' in this example can be liver, tumor or marrow. (c) A photograph of an assembled embodiment of the microfluidic device. Dye was used for visualization of channels. Dye was also mixed with the alginate hydrogel encapsulating the cultured cells in the cell culture chambers. (d) Assembly and cell seeding of a microfluidic device in which hydrogel-encapsulated cells are seeded into corresponding holes (chambers) on a cell culture chamber layer, and flattened with a porous polycarbonate membrane. Alginate gel is formed by wetting with calcium chloride solution for 30 minutes. After gel formation, the membrane is removed and the channel layer is closed on top, and the top layer is closed for sealing.

FIGS. 2a-b. (a) Medium recirculation with gravity-induced flow in an embodiment of the microfluidic device (also referred to herein as a microscale cell culture analog (μCCA)). Tilting of the device causes liquid to flow from one well to the other well. In one embodiment, after three minutes, the rocking platform changes the angle and medium flows in the opposite direction. (b) A plot of measured flow rates against various height differences (h).

Figure 3:
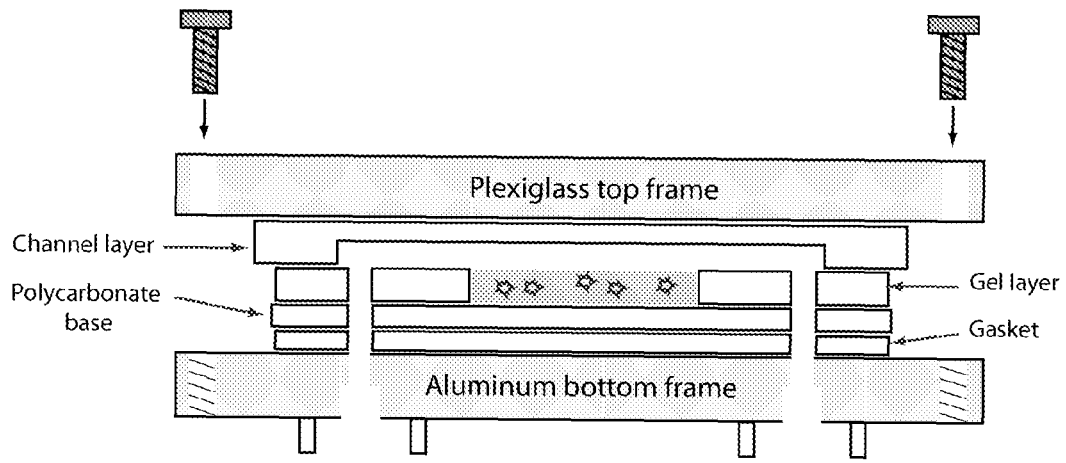

FIG. 3. Cross-sectional view of an embodiment of the microfluidic device after assembly. For gravity-induced flow or static flow, the device is flipped (see also FIGS. 2a, 4 and 5) and operated with the top frame on the bottom. For pump perfusion, the device is preferably used right side up, in the orientation shown here.

Figure 4:
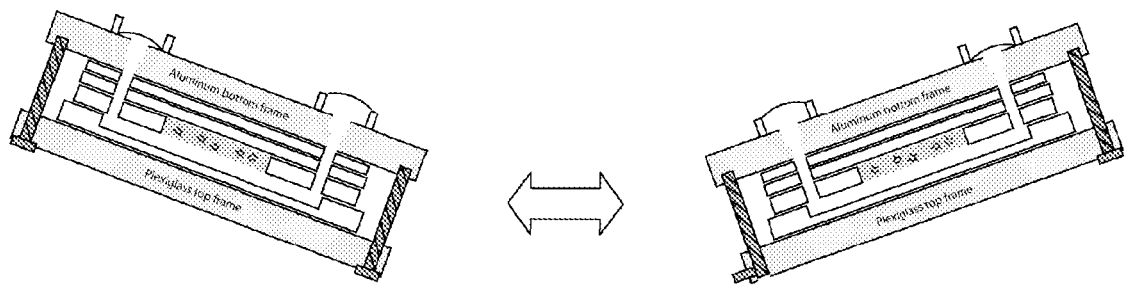

FIG. 4. Operation of an embodiment of the microfluidic device with gravity-induced flow. Cell culture medium is induced to flow through the channels by tilting the device back and forth on a rocking platform. The flow rate and the residence times can be controlled by adjusting the channel dimensions and the frequency of rocking.

Figure 5:
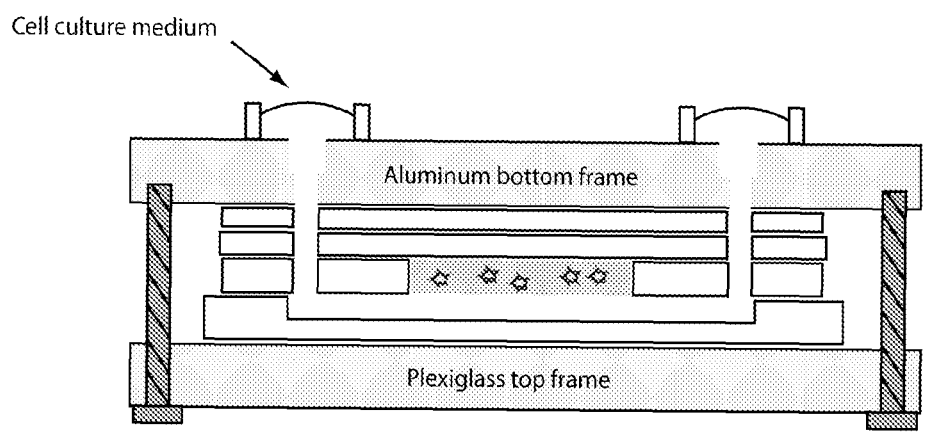

FIG. 5. Cross sectional view of an embodiment of the microfluidic device in orientation for gravity-induced or static mode operation (with the top frame on the bottom). Cell culture medium is placed inside the cell culture chambers via holes in the aluminum bottom frame (here oriented on top) and nutrients are supplied by passive diffusion.

FIGS. 6a-c. Live/dead staining of (a) HepG2/C3A (b) HCT-116 and (c) Kasumi-1 cells in a μCCA after three days of operation with medium recirculation using the gravity flow method of fluid circulation.

FIGS. 7a-c. Measured and simulated cell viability for three days in static conditions. (a) HepG2/C3A (b) HCT-116 and (c) Kasumi-1 for four different concentrations of 5-fluorouracil (5-FU) (0, 0.1, 0.2, and 0.5 mM).

FIGS. 8a-d. (a) Predicted concentration profiles of 5-FU in a μCCA for three different dosages. Measured (dots) and simulated (lines) viability of (b) HepG2/C3A, (c) HCT-116 and (d) Kasumi-1 cells in a μCCA treated with four different 5-FU concentrations for three days (0, 0.1, 0.2, 0.5 mM).

FIGS. 9a-b. (a) Viability of three cell lines after 3-day treatment with 5-FU alone or 5-FU plus uracil in a μCCA, encapsulated in 2% alginate. (b) Viability of three cell lines after 3-day treatment with 5-FU alone or 5-FU plus uracil. Cells were encapsulated in MATRIGEL® biological cell culture substrate in a μCCA.

FIGS. 10a-d. (a) Predicted concentration profiles of 5-FU in a μCCA at two dosing conditions. Inclusion of uracil prevents rapid degradation of 5-FU. (b) Predicted viabilities of three cell lines treated with 5-FU alone or 5-FU plus uracil. (c) Predicted concentration profiles of 5-FU in a μCCA at two dosing conditions (5-FU alone and 5-FU plus uracil), with the rate of 5-FU metabolism reduced three-fold. (d) Predicted viabilities of three cell lines with the reduced metabolic activity.

FIGS. 11a-c. (a) A bright-field photomicrograph of an assembled embodiment of the μCCA. A cell culture chamber and channels are shown on the left side of the picture. (b) A fluorescein solution was inserted to visualized the channels and test sealing. Channels are shown as horizontal stripes across the photomicrograph. Fluorescein also diffuses into alginate, staining it light green (shown as light gray in the photomicrograph). (c) A cell culture chamber is visualized with red fluorescent beads (appearing as bright spots in the photomicrograph), which were mixed with alginate and inserted into the μCCA.

FIGS. 12a-b. Live/dead staining result of cells cultured in a μCCA for five days with daily medium change. (a) Live. (b) Dead.

FIGS. 13a-d. The effect of recirculation mode on the pharmacokinetic profile of a prodrug (A) and a drug (B), with a simple conversion reaction A→B. (a) Continuous, closed-loop circulation mode. (b) Reciprocated circulation mode. (c) Concentration of a prodrug (A). (d) Concentration of a drug (B), generated from a prodrug.

5. DETAILED DESCRIPTION OF THE INVENTION

A microfluidic device for culturing cells, also referred to herein as a microscale cell culture analog (μCCA), is provided. In a preferred embodiment, the microfluidic device can be used for integrated pharmacokinetic-pharmacodynamic (PK-PD) analyses of drugs and for testing the toxicity of drugs, chemical compositions and other compounds of interest. The microfluidic device facilitates high-throughput operation and can be used for drug discovery. The design and mode of operation of the microfluidic device allows multiple cell lines to be cultured in a physiologically relevant environment.

In one embodiment, the microfluidic device can be flipped top-to-bottom 180° from the assembled orientation (FIGS. 2a, 4 and 5) and use gravity-induced fluidic flow, which eliminates the need for a pump and prevents formation of air bubbles. In one embodiment, the microfluidic device can comprise a minimum of a pair of fluidically connected reservoirs ("double reservoirs") or wells for cell culture medium. The microfluidic device can use reciprocating motion in the pair of reservoirs to replace either internal or external pumps for effecting microfluidic flow in microfluidic channels. In one embodiment, the fluid flow induced by the reciprocating motion simulates blood flow.

Since the design of the microfluidic device eliminates air bubble formation, its design significantly reduces bacterial contamination and enables high throughput implementation by eliminating the external pump found in currently available microfluidic devices.

The microfluidic device can also be run in static mode (FIG. 5) or with a pump (FIG. 3).

For clarity of disclosure, and not by way of limitation, the detailed description of the invention is divided into the subsections set forth below.

5.1 Microscale Cell Culture Apparatus (μCCA)

A microfluidic device for culturing cells is provided, also referred to herein as a microscale cell culture apparatus (μCCA). FIG. 1a and 3 show schematics of embodiments of the microfluidic device and its components. FIGS. 2a, 4 and 5 show schematics of embodiments of the microfluidic device that are flipped 180° top-to-bottom.

In one embodiment, the microfluidic device comprises a base (also referred to herein as a "base layer"), a cell culture chamber layer (also referred to herein as a "chamber" layer) and a fluidic channel layer (also referred to herein as a "channel layer").

The base layer can comprise any suitable polymer or plastic known in the art such as polycarbonate, PMMA or TEFLON® (polytetrafluoroethylene (PTFE)).

The cell culture chamber layer and/or the channel layer can comprise any material known in the art suitable for cell culture chambers or wells, e.g., PDMS (polydimethylsiloxane)), silicone, polystyrene or SU-8.

The cell culture chamber layer can comprise one or more cell culture chambers formed or integrated within the cell culture chamber layer. Cells are placed in the cell culture chamber layer. In one embodiment, the cells cultured in the cell culture chamber layer are encapsulated, e.g., in a hydrogel. Any hydrogel or other suitable matrix material known in the art can be used to encapsulate cells to be cultured in the microfluidic device, e.g., alginate, collagen, MATRIGEL® biological cell culture substrate, PEG (polyethylene glycol) or PVA (polyvinyl alcohol). In another embodiment, the cells cultured in the cell culture chamber layer are not encapsulated but may be cultured on other matrices (collagen, laminin) or scaffolds.

In a specific embodiment, shown in FIGS. 1a and 1c, the cell culture chamber layer is a 0.2 mm thick silicone layer with three through holes forming the cell culture chambers (once assembled with the fluidic channel layer, the through holes form a cell culture chamber with the top formed by the fluidic channel layer).

The fluidic channel layer (also referred to herein as a "channel layer") comprises a plurality of fluid channels that are interconnected in a network and positioned between the top (upper) frame and the cell culture chamber layer (FIG. 1a). In a specific embodiment, the fluidic channel layer comprises PDMS.

The channels of the fluidic channel layer are inwardly positioned, facing towards the cell culture chamber layer and the interior of the microfluidic device relative to the top and bottom frames (i.e., facing down/away from the top frame and the top of the device, and facing towards the bottom frame and the bottom of the device). In certain embodiments, the geometry of each channel can be individually designed to simulate a desired blood flow (discussed in more detail below), e.g., to mimic the blood flow circulation to an organ or tissue of interest.

The cell culture chamber layer is positioned between the fluidic channel layer and the base layer so that the cell culture chambers are fluidically connected to (and facing towards) the channels of the fluidic channel layer.

Circulation of the cell or tissue culture medium is achieved through the separate channel layer which is placed on top of the cell culture chamber layer.

In one embodiment, the fluidic channel layer and the cell culture chamber layer are separated, which allows for seeding of multiple three-dimensional (3-D) hydrogel-cell cultures. After seeding, the microfluidic device can be sealed. The combination of preformed 3-D hydrogel cultures and pumpless operation (see below) greatly facilitates easy setup and operation of the microfluidic device as a µCCA. This setup allows the device to be opened after it has started operating (if desired), to be resealed sterilely, and then to resume or continue operating.

In another embodiment, the microfluidic device further comprises a gasket. The gasket can be composed of any suitable sealing or gasket material known in the art, such as silicone. In one embodiment, the gasket is positioned on the interior surface of the bottom frame (FIGS. 1a and 3) between the bottom frame and the base. The gasket can be used to seal the microfluidic device.

In another embodiment, the microfluidic device further comprises a bottom (lower) frame beneath the base layer or the gasket and/or a top (upper) frame above the channel layer (FIGS. 1a and 3).

The bottom frame and the top frame can comprise any suitable material known in the art, preferably a lightweight, non-corroding or inert material such as aluminum, polymers, plastics, polycarbonate, or PLEXIGLAS® (polymethyl methacrylate (PMMA)).

In a specific embodiment, the µCCA device comprises an aluminum bottom frame and a polymethyl methacrylate (PMMA, PLEXIGLAS®) top frame (FIGS. 1a and 3).

In a specific embodiment, the microfluidic device comprises: an aluminum bottom frame, a silicone gasket, a plastic base layer, a PDMS cell culture chamber layer (in which cells, encapsulated in hydrogel, other matrices or not encapsulated, are placed), a PDMS channel layer, and plastic top frame, which are stacked and fastened with fasteners such as screws (FIGS. 1a and 3).

In another embodiment, the microfluidic device further comprises fasteners such as screws or clamps that align and fasten and/or seal the stacked components of the microfluidic device together (FIGS. 1a and 3). Any suitable fastener known in the art can be used.

The bottom frame, the gasket, the base layer, the cell culture chamber layer, the channel layer, and/or the top frame can have inlet and outlet holes. These holes can be aligned with the corresponding holes of the other components to allow circulation of the cell or tissue culture medium (FIGS. 3, 4 and 5).

In another embodiment, the microfluidic device can comprise a pair of fluidically connected reservoirs or wells for cell culture medium (e.g., a cell or tissue culture medium). FIGS. 2a, 4 and 5 show embodiments of the microfluidic device in which two fluidically connected wells ("double reservoirs") are shown holding droplets of cell culture medium) into which cell culture medium can be introduced or accumulate.

In another embodiment, the reservoir or well can be associated with an inlet hole or an outlet hole.

In another embodiment, the microfluidic device can comprise a two- or three-dimensional cell culture matrix (see the section entitled "Cell Culture" for more details).

In a specific embodiment, the microfluidic device comprises an aluminum bottom frame, a silicone gasket, a plastic base layer, a PDMS cell culture chamber layer, a PDMS channel layer, and a plastic top frame, which are stacked and fastened with screws (FIG. 3).

In the cell culture experimental model shown in FIG. 1b, hydrogel-encapsulated cells representing liver (hepatoma, HepG2/C3A), tumor (colon cancer, HCT-116) and bone marrow (myeloblasts, Kasumi-1) are cultured in each chamber. The cell culture chamber layer is placed on top of a polycarbonate base layer. Between the polycarbonate base layer and the bottom aluminum frame, a 0.5 mm silicone gasket (Grace Bio Labs) is placed (FIG. 1a).

An optical fiber or other microscale optical device can be used to monitor the real-time performance of the microfluidic device, e.g., when it is moving. Such monitoring methods are known in the art.

5.2 Microfluidic Device Operation

Operation of the microfluidic device can be achieved in at least three different modes. Cell culture medium is preferably perfused by using gravity-induced flow (gravity flow mode) (FIGS. 2a and 4), mimicking the blood circulation in the human body. Cell culture medium can also be perfused by passive diffusion (static mode) or by using a peristaltic pump (pump perfusion mode).

In gravity flow mode (FIGS. 2a and 4), the microfluidic device is operated in flipped (180° top-to-bottom) orientation. Cell culture medium is introduced into the cell culture chambers and gravity flow is induced by tilting the device back and forth periodically. The flow rate through the channels will depend on the frequency of the rocking (gravity flow mode). The flow rate is determined by the speed and angle of rocking and the geometry of fluidic channels. If the speed and angle of rocking and the geometry of fluidic channels are kept constant, the flow rate will also be constant. By varying the geometry of one channel in relation to another, the microfluidic device can be configured so that it has different flow rates in different cell culture chambers. Such calculations of flow rate are known in the art.

In a preferred embodiment, the microfluidic device uses gravity-induced fluidic flow. This eliminates the need for a pump and prevents formation of air bubbles. The microfluidic device can comprise one or more pairs of wells or reservoirs ("double reservoirs") that are fluidically connected. Reciprocating motion can be used in the pair of reservoirs to replace either internal or external pumps for effecting microfluidic flow in the channels (FIG. 4).

Gravity-induced flow can be effected by tilting the device on a rocking platform (FIGS. 2a and 4). Culture medium is placed in, e.g., two separate wells. The rocking platform provides a reciprocating motion and the medium flows in and out of the wells. The flow pattern can be examined by mathematical simulation. It has been verified that this reciprocating motion provides pharmacokinetic profiles of a drug in each chamber (organ) similar to those observed with recirculation using an external pump. The time it takes for one loop of recirculation can be controlled by changing the frequency of rocking platform. This mode of operation eliminates the need for a pump to introduce flow.

The flow pattern induced in the microfluidic device by reciprocating motion is similar to those of microfluidic devices using a pump. The elimination of bubble formation in the microfluidic device is accomplished using gravity induced flow and reciprocating motion in the microfluidic device.

Bubble formation is a common problem for many currently available microfluidic devices with pumps. The mode of operation for the microfluidic cell culture device using gravity-induced flow and periodic rocking motion enables bubble-free operation. Flow is directed downward, which prevents air from flowing into the device together with the medium. This is important because bubble formation in a microfluidic device is a notorious problem, and this mode of operation essentially eliminates the possibility of bubble problem.

Gravity induced flow and static modes of operation (described below) eliminate the need of a pump for the operation of the device, which simplifies the system and enables high-throughput operation of the device.

In one embodiment, this pumpless microfluidic flow simulates blood circulation.

The microfluidic device can also be run in static mode in a flipped orientation (180° top-to-bottom) from the assembly orientation. In static mode (FIG. 5), the assembled device is placed upside down and cell culture medium is placed in the wells in the bottom aluminum frame. The medium diffuses into the channels and gels, without active perfusion (static mode).

The microfluidic device can also be run with a pump, preferably in a right side up orientation (FIG. 3). In pump perfusion mode, tubing is connected through the inlet and outlet holes and cell culture medium is perfused into the channels by using a pump. Either a syringe pump can be used for single-pass perfusion, or a peristaltic pump can be used for circulation of medium (pump perfusion mode).

The channel layer can comprise an array of fluidic channels with defined thickness and height. This defined geometry is one factor that determines the flow rate through the fluidic channels. Another factor that determines the flow rate through the fluidic channels is speed and angle of rocking. The ability to control the thickness of the cell culture chamber layer and/or the channel layer, together with the control of rocking angle and flow rates through the fluidic channels gives a precise control of mass transfer of nutrients and oxygen for better mimicking of physiological environment. Culturing multiple cell types representing different organs in the human body allows the study of pharmacokinetic-based study of drugs with multi-organ interaction while 3-D hydrogel cell culture provides a more physiologically realistic environment than 2-D cell culture.

In one embodiment, the channel layer can be used (prior to device assembly) as a substrate for culturing endothelial cells lining the blood vessel, which gives a structure resembling the native tissue environment with blood vessels. The separation of the cell culture chamber layer and the channel layer allows a straightforward implementation of tissue-like structure with blood flow. Endothelial cells can be cultured on the channel layer prior to the device assembly, and by overlaying the channel layer on top of the cell culture chamber layer, a physiological model of tissue with blood vessels lining the tissues can be created.

Preferably, the geometry of the fluidic channel in the channel layer that is fluidically connected to a selected cell culture chamber is designed to mimic the relative blood flow distribution to a selected organ or tissue of interest in the human body or the body of another organism (e.g., a mammal) of interest.

The relative blood flow distribution to a selected organ or tissue of interest in the human body are well known in the art, e.g., 58%, 18%, and 24% into the liver, tumor, and the marrow compartment, respectively (J. H. Sung and M. L. Shuler, Lab Chip, 2009, 9, 1385-1394; B. Davies and T. Morris, Pharm. Res., 1993, 10, 1093-1095).

The design and mode of operation of the microfluidic device allows multiple cell lines to be cultured in a physiologically relevant environment. The microfluidic device eliminates air bubble formation, significantly reduces bacterial contamination and enables high throughput implementation by eliminating the external pump found in currently available microfluidic devices.

5.3 Cell Culture

The geometry of the cell culture chamber layer and matrices (their shape and thickness), as well as the geometry of the channel layer, influences the circulation of cell or tissue culture medium and enables creation of a physiologically realistic tissue environment. The geometry of the fluidic channels in the channel layer can be precisely controlled using soft lithography techniques. Together with the control of cell matrix geometry, control over transport of oxygen and nutrients to the cultured cells can be achieved. The geometries of the cell culture chamber layer and the channel layer can be controlled separately for each organ to mimic the specific physiological parameters for the organ, such as residence times, flow rates, and the size of the tissue. For example, a single device can contain separate liver, lung, and tumor cell culture chambers, and the flow rates and the sizes of the hydrogels in each chamber can be controlled to be similar to the physiological values in the human body.

The microfluidic device can comprise one or more two-dimensional (2-D) or, preferably, three-dimensional (3-D) matrices in the cell culture chamber layer, positioned in one or more of the culture chambers, for culturing cells.

Cells can also be cultured in free suspensions or encapsulated in any suitable hydrogel for cell culture known in the art (e.g., alginate) or other matrices or scaffolds. In certain embodiments, cells cultured in the cell culture chamber layer are encapsulated by a hydrogel and can be easily recovered after experiment for further analysis, since they are encapsulated by the hydrogel.

Methods for culturing cells in the microfluidic device are also provided. Cells or tissues can be cultured encapsulated in a hydrogel, other matrix, unencapsulated or on a scaffold. Any cell or tissue of interest can be cultured. For example a cell can be normal, mutant, cancerous or diseased. The cell can be derived from any unicellular organism known in the art (e.g., bacteria, protists) or multicellular organism (e.g., animal, plant, etc). The tissue can be derived from any multicellular organism. The cultured cells or tissues can be a single cell or tissue type or a plurality of cell and/or tissue types.

One or more cell or tissue types can be cultured simultaneously in the microfluidic device. A single cell or tissue type can be cultured separately in separate culture chambers, or more than one cell or tissue type can be cultured in a chamber.

In one embodiment, different types of cells or tissues representative of the body (e.g., human or mammalian) can be cultured, e.g., heart, kidney, liver, lung, heart, stomach, intestines, brain, neurons, glia, pancreas, ovary, muscle (skeletal, cardiac, smooth, etc.), skin, etc.

Multiple cell or tissue types can be cultured as a co-culture embedded in the one or more two-dimensional (2-D) or three-dimensional (3-D) cell matrices (e.g., hydrogel matrices) in the cell culture chamber layer. In one embodiment, one or more cell or tissue types can be cultured encapsulated and/or co-cultured with other cell types that are not encapsulated (e.g., growing on the outside of the encapsulated cells or in a suspension). The cell matrices can comprise any hydrogel or other suitable material for cell culture known in the art and can be constructed using standard methods known in the art. Cells can also be grown on scaffolds using methods known in the art.

Matrices can have controlled thickness. The geometry (shape and thickness) of the 3-D matrices can be controlled by using an elastic mold that defines the geometry of the matrix.

In one embodiment, by employing a mold for holding the matrices, the thickness of 3-D hydrogel matrices can be precisely controlled from less than 100 micrometer to several millimeters.

5.4 Fabrication of the Microfluidic Device

The components of the microfluidic device, e.g.., the bottom frame, the gasket, the plastic base layer, the cell culture chamber layer, the channel layer and the top frame, can be fabricated using methods known in the art.

For the embodiment shown in FIG. 1a, the master for the channel layer was fabricated using conventional soft-lithography techniques. SU-8 2075 (MicroChem, Newton, Mass.) of 225 mm thickness was spin-coated on a silicon wafer by spinning at 300 rpm for 30 s, and was baked at 65° C. for 5 min and at 95° C. for 45 min. The pattern was exposed to SU-8 at 650 mJ cm$^{-2}$ using an EVG620 contact aligner (EV Group, Tempe, Ariz.). Then a post-exposure bake was done at 65° C. for 1 min and 95° C. for 15 min, and the master was developed in a SU-8 developer solution for 12 min. The aluminum bottom and PLEXIGLAS® top frames were made with a milling machine. The bottom frame also has two inlet/outlet holes (~2 mm diameter) at each corner. The cell culture chamber layer was made by curing a 5 mm thick PDMS sheet, cutting it to 1 cm by 1 cm size, and punching a 4 mm through hole with a biopsy punch. The PDMS well was fixed with biocompatible, non-toxic glue (Epotek 301-2, Epoxy Technology, Billerica, Mass.).

5.5 Microfluidic Device Assembly and Set-Up

Methods for assembling the microfluidic device are provided. In one embodiment, the microfluidic device can be assembled by sandwiching a cell culture chamber layer and a fluidic channel layer. Prior to assembly, a cell culture chamber in the cell culture chamber layer is not fluidically connected to the fluidic channels in the channel layer because the cell culture chamber and the fluidic channel are in separate layers. A physical connection between a cell culture chamber in the cell culture chamber layer and one or more of the fluidic channels in the channel layer is not made until the cell culture chamber layer and the channel layer are sandwiched together with the fluidic channels of the channel layer facing towards the cell culture chambers in the cell culture chamber layer. By sandwiching the two layers, the one or more cell culture chambers in the cell culture chamber layer become functionally and (once fluid is added to the device) fluidically connected to one or more fluidic channels in the channel layer.

The assembled cell culture chamber layer and channel layer can be sandwiched between the bottom frame and the top frame. A gasket (e.g., silicone) and a base (e.g., polycarbonate) can be added to ensure better sealing.

In one embodiment, the method for assembling the microfluidic device comprises providing a bottom frame (e.g., aluminum), a gasket (e.g., silicone), a base (e.g., polycarbonate) and a cell culture chamber layer; placing the gasket on top of the bottom frame; placing the base on top of the gasket; and placing the cell culture chamber layer on top of the base. To prevent wrinkling of thin cell culture chamber layer (e.g., 0.25 mm thick), a drop of 95% ethanol can be placed on top of the base before placing the cell culture chamber layer on the base, and can be evaporated in a hot oven. In one embodiment, the assembled bottom frame, gasket, base, and cell culture chamber layer can be sterilized by autoclaving or other method for sterilization known in the art.

Cells, e.g., in a cell suspension, can be placed in a cell culture chamber in the cell culture chamber layer (FIG. 1d). In one embodiment, cells are suspended or encapsulated in a hydrogel (e.g., alginate). A filter, e.g., a porous polycarbonate membrane filter (8 μm pore size, VWR Scientific, West Chester, Pa.) can be placed on top to flatten the cell suspension. Sterile filtered 30 mM calcium chloride solution can be applied onto each cell chamber to polymerize the hydrogel. After 30 minutes of incubation at room temperature, calcium chloride solution and the membrane filter can be removed.

The method can also comprise the steps of providing a fluidic channel layer and placing the fluidic channel layer on top of the cell culture chamber layer with the channels facing down. In one embodiment, the top surface of the cell culture chamber layer can be flooded with 1 ml of DPBS, and the fluidic channel layer was placed on top of the cell culture chamber layer with the channels facing down. Once the channels are facing down towards the cell culture chamber layer, the channels are closed and fluidically connected to the cell culture chambers (FIG. 1d).

The method can also comprise the steps of providing a top frame and placing the top frame on the fluidic channel layer. The method can also comprise the step of closing or sealing the microfluidic device (FIG. 1d). In one embodiment, the method comprises fastening the bottom frame, the gasket, the base layer, the cell culture chamber layer, the channel layer and the top frame with fasteners (e.g., screws).

As described above, the microfluidic device is simple to assemble. It also has a short set up time that is greatly reduced compared with currently available microfluidic cell culture systems. The microfluidic device of the invention takes about 2 hours to set up, as opposed to 12 or more hours for currently available microfluidic cell culture systems.

The method used for assembling the device can significantly reduce the time necessary to seed cells and assemble the devices. It takes approximately 2 hours for seeding cells and assembling 12 devices, excluding the time needed for preparation of materials and autoclaving them before start.

By contrast, using presently available chip-based cell culture systems, one seeds cells in the chamber and incubate the chips overnight in an incubator so that cells fully attach to the surface. The assembly process takes approximately 2-3 hours, because it is necessary to flush the tubing extensively prior to the start of assembly process to make sure no bubbles are present in the tubing. Even after excluding the time needed for cell attachment, it takes about 5 hours to flush the whole system, assemble 8 devices and connect them to tubing.

In the present microfluidic device the flushing step is no longer necessary.

Owing to the configuration of the present device, it can be opened during the course of a run, conditions manipulated or altered within the device (e.g., cells added or removed; media, chemicals, drugs, factors, agents etc. added or removed) and resealed, and the run continued.

5.6 Uses and Advantages of the Microfluidic Device

The microfluidic device can be used to perform pharmacokinetic and/or pharmacodynamic studies of the effects on the cultured cells of drugs, toxins and other chemical agents. Such analyses are described in detail in Section 6.

An integrated pharmacokinetic-pharmacodynamic (PK-PD) model can be developed by constructing a PK and PD model separately, and then combining the two. A PK model has the same layout of compartments as a μCCA device. A PD model is integrated into each compartment, describing the kinetics of cell death in each organ. To construct a PK model for a μCCA, mass balance equations describing the flow in, flow out, and metabolism are set up for each compartment, and the ordinary differential equations (ODEs) are solved numerically. Solving the equations requires several parameters, such as physiological parameters (flow rate and size of chambers) and enzyme kinetic parameters for the metabolism of the drug, chemical or therapeutic agent of interest.

In one embodiment, the microfluidic device and methods provided can be used as a pharmacokinetic-pharmacodynamic (PK-PD) based platform for testing the toxicity of chemical compositions, drugs and other compounds of interest.

In one embodiment, the microfluidic device is used for conducting a pharmacokinetic, a pharmacodynamic or a pharmacokinetic-pharmacodynamic (PK-PD) analysis of an effect of an agent (e.g., drug, chemical composition or toxin) of interest on cultured cells. The in vitro pharmacokinetic or pharmacodynamic value can be comparable to the in vivo pharmacokinetic or pharmacodynamic value for a cell or tissue type of interest. In another embodiment, the in vitro pharmacokinetic or pharmacodynamic value is 0.01 to 0.1×, 0.1× to 1×, 1×-10×, 10×-100×, 100×-1000× or greater than 1000× the in vivo pharmacokinetic or pharmacodynamic value.

In another embodiment, the method comprises the step of performing an analysis or assay of an effect of an agent of interest on the cultured cells or tissue, thereby determining an in vitro effect of the agent of interest on the cultured cells or tissue. In another embodiment, the in vitro value of the effect is comparable to the in vivo value of the effect for a cell or tissue type of interest. In another embodiment, the in vitro value is 0.01 to 0.1×, 0.1× to 1×, 1×-10×, 10×-100×, 100×-1000× or greater than 1000× the in vivo value.

In another embodiment, the microfluidic device is used for high throughput applications, since a greater number of the microfluidic devices can be placed in a smaller footprint within an incubator due to the microfluidic device's compactness and non-reliance on a pump. Using reciprocating motion and a fluidically connected pair of reservoirs to replace an external or internal pump allows having many devices in the limited space of an incubator. Reduced time for set up allows assembling more devices in the limited time period. For example, taking too long time for assembly of the device could have a negative impact on cell viability.

The microfluidic device can be autoclaved and can be reversibly assembled and disassembled in a sterile manner. This feature allows researchers to retrieve the cells from the device for further examination (for example, gene expression), to replace the cells with different cells in the middle of experiment, while maintaining sterility, to add a factor to cells currently in the microfluidic device, and/or continue a run in the device. This is not possible with many current microfluidic systems, since they are sealed in an irreversible manner.

The microfluidic device is designed so that the process of cell seeding and the device assembly is simple, making it a more robust system that other currently available microfluidic devices. The length of time required to seed the cells and assemble the microfluidic device requires approximately 2-3 hours, significantly less that the 2 days for other devices. This system is more robust in terms of unwanted air bubble formation, medium leakage and bacterial contamination, which have been major limiting factors in achieving stable, high-throughput operation of the device.

The microfluidic device and the methods based on the device disclosed herein allow much more robust, easier, and more efficient operation of a cell culture microfluidic device with medium recirculation.

Currently available microfluidic cell culture systems have complicated components and their use requires highly-trained personnel to achieve meaningful results. By contrast, personnel can be easily trained to use the microfluidic device of the invention. After a short training period of about two hours regarding how to assemble and operate the device, personnel are typically able to use the device without difficulty.

The microfluidic device has many applications in drug discovery and therapeutics. It can be used as a platform for testing the effect of drugs on various target organs simultaneously. For example, lung cells and liver cells can be cultured inside the device and the test drug can be added to the circulating medium, and the lung and liver toxicity can be tested by measuring the viability of the lung and liver cells.

The microfluidic device can be used as a platform for testing the effect of a drug and its metabolites simultaneously, in pharmacokinetic-based way. Liver cells are cultured in one of the chambers, which can metabolize the test drug to metabolites, which will circulate to other chambers to exert any effect on the target cells. By controlling the dimensions of the channels, the flow rates and residences times of circulating medium can be adjusted to be similar to human physiological values.

The microfluidic device can be used for tissue-engineering purposes, since it enables an easy control of transport of nutrients and oxygen, and the geometry of the tissue construct. The easy control of the gel thickness enables a control of transport process inside the gel and the concentration gradients of nutrients and oxygen to create cellular microenvironments similar to native tissue.

In one embodiment, a method for culturing cells for tissue engineering is provided. The method can comprise the steps of:
  providing the microfluidic device of the invention;
  placing the cells to be cultured in the microfluidic device; and
  culturing the cells, wherein the culturing step comprises flowing cell culture medium through the microfluidic device; and
  harvesting the cultured cells.

The microfluidic device can be used as an experimental model for angiogenesis of tumor tissue, since endothelial cells lining the blood vessels can be cultured on the surface of the channel layer, and tumor cells can be cultured in hydrogel matrix in the cell culture chamber layer, providing environment similar to the tumor tissue with adjacent blood vessels, with controllable distance between tumor tissue and the blood vessels, and controllable tumor size, and flow rates through the blood vessels. The microfluidic device disclosed herein is the first known attempt to combine a microfluidic system with an integrated PK-PD modeling approach to achieve a PK-PD 'model-on-a-chip' (FIG. 1a). This combined approach of an in vitro/in silico systems enables prediction of drug toxicity in a more realistic manner than conventional in vitro systems.

6. EXAMPLES

6.1 Example 1

Microfluidic Device for a
Pharmacokinetic-Pharmacodynamic (PK-PD) Model
on a Chip Drug discovery is often impeded by the poor predictability of in vitro assays for drug toxicity. One primary reason for this observation is the inability to reproduce the pharmacokinetics (PK) of drugs in vitro. Mathematical models to predict the pharmacokinetics-pharmacodynamics (PK-PD) of drugs are available, but have several limitations, preventing broader application. This example demonstrates a microscale cell culture analog (µCCA), a microfluidic device based on a PK-PD model, in which multiple cell culture chambers are connected with fluidic channels to mimic multi-organ interactions. The µCCA can be used to test drug toxicity in a pharmacokinetic-based manner.

One critical issue with microfluidic devices is that specialized techniques are required for assembly and operation, limiting its usability to non-experts. The µCCA demonstrated in this example has enhanced usability while allowing cell or tissue cultures of multiple types in multiple formats (cell suspensions, encapsulated cells, 2-D or 3-D matrices). Gravity-induced flow enables pumpless operation and prevents bubble formation. Three cell lines representing the liver, tumor and marrow were cultured in the three-chamber µCCA to test the toxicity of an anticancer drug, 5-fluorouracil (5-FU). The result was analyzed with a PK-PD model of the device, and compared with the result in static conditions. Each cell type exhibited differential responses to 5-FU, and the responses in the microfluidic environment were different from those in static environment. Combination of a mathematical modeling approach (PK-PD modeling) and an in vitro experimental approach (µCCA) provides a platform with improved predictability for testing drug toxicity and can help researchers gain a better insight into the drug's mechanism of action.

6.1.1 Introduction

A microscale cell culture analog (µCCA), also known as 'body-on-a-chip', is a microfluidic device known in the art for PK-based drug toxicity testing (R. Khamsi, Nature, 2005, 435, 12-13; A. Sin, K. C. Chin, M. F. Jamil, Y. Kostov, G. Rao and M. L. Shuler, Biotechnol. Prog., 2004, 20, 338-345). Multiple cell types representing different organs are cultured in separate chambers on a single chip, interconnected by channels mimicking the blood flow pattern. The fluid pattern in the µCCA is precisely calculated and fabricated to mimic the blood circulation. The µCCA has been used to test the metabolism dependent toxicity of naphthalene, doxorubicin, and tegafur (K. Viravaidya, A. Sin and M. L. Shuler, Biotechnol. Prog., 2004, 20, 316-323; J. H. Sung and M. L. Shuler, Lab Chip, 2009, 9, 1385-1394; D. A. Tatosian and M. L. Shuler, Biotechnol. Bioeng., 2009, 103, 187-198).

The µCCA is based on the concept of a mathematical model, known as a physiologically based pharmacokinetic (PBPK) model. The term, pharmacokinetics (PK), refers to a time dependent concentrations of a substance in a living system (L. E. Gerlowski and R. K. Jain, J. Pharm. Sci., 1983, 72, 1103-1127). A PBPK model is built on physiological considerations, where the human body is segregated into separate compartments representing organs, connected by the blood circulation. A PBPK model allows one to predict the concentration profiles of a drug and its metabolites from a given dose. Being the physical realization of a PBPK model, a µCCA is an ideal in vitro platform for the mathematical modeling approach (A. Ghanem and M. L. Shuler, Biotechnol. Prog., 2000, 16, 334-345).

Pharmacodynamics (PD), which differs from PK, refers to the pharmacological effect of a drug, with the assumption that the observed effect is a function of a drug concentration. A PD model predicts the pharmacological effect (for example, death of tumor cells in response to a chemotherapeutic agent), from a drug concentration at the target site (D. E. Mager, E. Wyska and W. J. Jusko, Drug Metab. Dispos., 2003, 31, 510-518). Pharmacokinetics and pharmacodynamics can be combined to create an integrated PK-PD model, which can predict the time-course of pharmacological effects from a dosage (H. Derendorf and B. Meibohm, Pharm. Res., 1999, 16, 176-185). For example, an integrated PK-PD model has been used to predict the growth kinetics of tumor in rats or mice, treated with chemotherapeutic agents (E. D. Lobo and J. P. Balthasar, J. Pharm. Sci., 2003, 92, 1654-1664; J. H. Sung, A. Dhiman and M. L. Shuler, J. Pharm. Sci., 2009, 98, 1885-1904). Combination of a PBPK model and a µCCA has been demonstrated (K. Viravaidya, A. Sin and M. L. Shuler, Biotechnol. Prog., 2004, 20, 316-323; A. Ghanem and M. L. Shuler, Biotechnol. Prog., 2000, 16, 334-345), but a combination of PK-PD model and a µCCA has not been demonstrated previously.

The present example demonstrates one embodiment of the invention, which is a combination of a PK-PD model and a µCCA. The µCCA is used in this example, in conjunction with PK-PD principles to quantitatively analyze the effect of a chemotherapeutic agent, 5-fluoro uracil (5-FU), combined with uracil. The major pathway for the metabolism of 5-FU is known to be through the enzyme dihydropyrimidine dehydrogenase (DPD), which is mainly present in the liver (A. B. Van Kuilenburg, R. Meinsma, L. Zoetekouw and A. H. Van Gennip, Int. J. Cancer, 2002, 101, 253-258). Uracil is a natural substrate of the enzyme DPD, and inhibits 5-FU metabolism by competitive inhibition. Uracil is often administered in combination with 5-FU or prodrugs of 5-FU, to improve the pharmacokinetics and the effect of 5-FU (J. S. de Bono and C. J. Twelves, Invest. New Drugs, 2001, 19, 41-59). The constructed PK-PD model was used to predict the effect of combining 5-FU with a modulator, uracil, and compare it with experimental results. This in vitro/in silico system, combining a microfluidic system with an integrated PK-PD modeling approach, can be used to predict drug toxicity in a more realistic manner than conventional in vitro systems.

6.1.2 Materials and Methods

Cell Culture and Chemicals

McCoy's SA medium, HEPES, sodium chloride, uracil, and 5-fluorouracil (5-FU) were purchased from Sigma Aldrich (St. Louis, Mo.). MEM medium, RPMI-1640 medium, live/dead viability/cytotoxicity kit, and fetal bovine serum (FBS) were purchased from Invitrogen (Carlsbad, Calif.). The colon cancer cell line, HCT-116, was obtained from American Type Culture Collection (ATCC, Manassas, Va.) and cultured in a T-flask in McCoy's SA medium (Sigma Aldrich) with 10% FBS (Invitrogen). A hepatoma cell line, HepG2/C3A (ATCC), was maintained in MEM medium (Invitrogen) with 10% FBS. Myeloblast cell line Kasumi-1 (ATCC) was maintained in RPMI-1640 medium (ATCC) with 20% FBS. All cell lines were cultured in a mammalian cell incubator maintained at 37° C. with 5% $CO_2$.

Design and Fabrication of a Microscale Cell Culture Analog (µCCA)

The embodiment of the µCCA device disclosed in this example comprised multilayers of PDMS (polydimethylsiloxane), sealed between an aluminum bottom and polymethyl methacrylate (PMMA, PLEXIGLAS®) top frames (FIG. 1a). Underneath the top PLEXIGLAS® top frame, a PDMS fluidic channel layer was placed with channels facing down. The geometry of the channels for each chamber was designed to mimic the relative blood flow distribution to selected organs of the human body (58%, 18%, and 24% into the liver, tumor, and the marrow compartment, respectively) (J. H. Sung and M. L. Shuler, Lab Chip, 2009, 9, 1385-1394; B. Davies and T. Morris, Pharm. Res., 1993, 10, 1093-1095).

The cell culture chamber layer was a 0.2 mm thick silicone layer with three through holes for cell culture chambers. Hydrogel-encapsulated cells representing the liver (hepatoma, HepG2/C3A), tumor (colon cancer, HCT-116) and the marrow (myeloblasts, Kasumi-1) were cultured in each chamber. The cell culture chamber layer was placed on top of a polycarbonate base, and between the polycarbonate base and the bottom aluminum frame, a 0.5 mm silicone gasket (Grace Bio Labs) was placed. The master for the channel layer was fabricated using conventional soft-lithography techniques. SU-8 2075 (MicroChem, Newton, Mass.) of 225 mm thickness was spin-coated on a silicon wafer by spinning at 300 rpm for 30 s, and was baked at 65° C. for 5 min and at 95° C. for 45 min. The pattern was exposed to SU-8 at 650 mJ cm$^{-2}$ using EVG620 contact aligner (EV Group, Tempe, Ariz.). Then post-exposure bake was done at 65° C. for 1 min and 95° C. for 15 min, and the master was developed in a SU-8 developer solution for 12 min. The aluminum bottom and PLEXIGLAS® top frames were made with a milling machine. The bottom frame also has two inlet/outlet holes (~2 mm diameter) at each corner. Medium reservoirs were made by curing a 5 mm thick PDMS sheet, cutting it to 1 cm by 1 cm size, and punching a 4 mm through hole with a biopsy punch. The PDMS well was fixed with biocompatible, non-toxic glue (Epotek 301-2, Epoxy Technology, Billerica, Mass.).

Device Assembly and Operation

The device was assembled by sandwiching a cell culture chamber layer and a fluidic channel layer between an aluminum bottom frame and a PLEXIGLAS® top frame. A silicone gasket and a polycarbonate base were added to ensure better sealing. The detailed steps of assembling the device are described in below in the section entitled "Incorporation of Hydrogel Cell Culture and Assembly of a μCCA." After assembly, the device was flipped upside-down, and two medium reservoirs were filled with medium. The device was placed on a rocking platform, set to change direction at approximately every 3 min. Desired concentrations of drugs (5-fluorouracil and uracil) were added to the cell culture medium.

The whole system was placed inside a cell culture incubator with 5% $CO_2$. After a specified amount of time, the device was dissembled and cells were retrieved by dissolving the alginate in a dissolving buffer (55 mM sodium citrate, 30 mM EDTA, 0.15M NaCl) for 30 min at 37° C., or from MATRIGEL® by dissolving in DPBS with 5 mM EDTA solution at 4° C. Cell viability was determined by Trypan-blue exclusion assay using a hemocytometer. At least triplicates were done for each data point.

Toxicity Experiment in Static Conditions

For static condition experiment, the same silicone gaskets were prepared on a glass slide, similar to the μCCA. Cells were seeded into the holes, encapsulated in hydrogel, and 300 ml of cell culture medium were placed on top. This volume is same as the volume of medium placed in the reservoir of a μCCA. Therefore, cells in static conditions are essentially the same as the cells in a μCCA, except that the device was not assembled with the channel layer, and cells were immersed in liquid medium. Cell viability was assessed using the same method as a μCCA.

Pharmacokinetic-Pharmacodynamic (PK-PD) Modeling

An integrated PK-PD model was developed by constructing a PK and PD model separately, and then combining the two. A PK model has the same layout of compartments as a μCCA device. A PD model is integrated into each compartment, describing the kinetics of cell death in each organ. To construct a PK model for a μCCA, mass balance equations describing the flow in, flow out, and metabolism were set up for each compartment, and the ordinary differential equations (ODEs) were solved numerically. Solving the equations required several parameters, such as physiological parameters (flow rate and size of chambers) and enzyme kinetic parameters for the metabolism of 5-FU and uracil, which are summarized in Table 1.

TABLE 1

Parameters for the PK model of a μCCA

| Name | Description | Value |
| --- | --- | --- |
| Physiological parameters[a] | | |
| V_L | Volume of liver chamber | 11.3 μl |
| V_T | Volume of tumor chamber | 11.3 μl |
| V_M | Volume of marrow chamber | 11.3 μl |
| V_B | Volume of medium reservoir | 300 μl |
| Q_L | Flow rate into liver chamber | 87.6 μl min$^{-1}$ |
| Q_T | Flow rate into tumor chamber | 26.7 μl min$^{-1}$ |
| Q_M | Flow rate into marrow chamber | 35.6 μl min$^{-1}$ |
| Enzyme kinetic parameters[b] | | |
| Vm_FU | Maximum rate of 5-FU metabolism | 2385 nmol min$^{-1}$ ml$^{-1}$ |
| Km_FU | Michaelis-Menten constant for 5-FU metabolism | 40 nM |
| Vm_U | Maximum rate of uracil metabolism | 1695 nmol min$^{-1}$ ml$^{-1}$ |
| Km_U | Michaelis-Menten constant for U metabolism | 40 nM |
| Ki_U[c] | Inhibition constant of uracil on 5-FU metabolism | 20 nM |
| Ki_FU[c] | Inhibition constant of 5-FU on uracil metabolism | 10 nM |

[a]Physiological parameters such as volumes and flow rates of organ chambers were determined based on reported values of organ sizes and blood flow rates in the human body (J. H. Sung and M. L. Shuler, Lab Chip, 2009, 9, 1385-1394; B. Davies and T. Morris, Pharm. Res., 1993, 10, 1093-1095).
[b]The enzyme kinetic parameters were calculated from the rate of 5-FU and uracil metabolism in a rat (K. Ikenaka, T. Shirasaka, S. Kitano and S. Fujii, Gann, 1979, 70, 353-359) and reported protein content and cell number in the liver (D. J. Quick and M. L. Shuler, Biotechnol. Prog., 1999, 15, 540-555). The reported rates of 5-FU and uracil in a rat and human are comparable F. N. Naguib, M. H. el Kouni and S. Cha, Cancer Res., 1985, 45, 5405-5412).
[c]Inhibition constants were taken from a previous study (J. H. Sung, A. Dhiman and M. L. Shuler, J. Pharm. Sci., 2009, 98, 1885-1904).

The details of sources for the parameters are summarized also. In a general form, the differential equation can be expressed as follows:

$$V_n \frac{dC_n}{dt} = Q_n C_B - Q_n C_n - R_n \quad (1)$$

where $C_n$ is the drug concentration in the liver, tumor or marrow compartment, $C_B$ is the concentration in the medium reservoir, $Q_n$ is the flow rate into the liver, tumor or marrow compartment, and $R_n$ is the rate of reaction occurring in the compartment. The ODEs for all compartments are set up, and the set of ODEs are solved using numerical methods. The predicted concentration profiles of 5-FU and uracil were used as inputs of a PD model in each compartment. To construct a PD model that predicts the response of cells to the drugs, a transit compartment model was used. A transit compartment model assumes a series of steps which cells go through to reach the final cell death stage. This type of model has been used to simulate the growth kinetics of tumors in response to chemotherapeutic agents (E. D. Lobo and J. P. Balthasar, AAPS PharmSciTech, 2002, 4, E42). This transit compartment model is useful for modeling the pharmacological effect of compounds that may be mediated by time-dependent transduction, and when there is a time lag in the final drug response (Y. N. Sun and W. J. Jusko, J. Pharm. Sci., 1998, 87, 732-737). It can be particularly useful for modeling the cell kill effect of chemotherapeutic agents, since chemotherapeutic agents exert their effects through a complex mechanism of action, and in many cases there is a time delay between the administration of the agents and the observation of the effect (E. D. Lobo and J. P. Balthasar, AAPS PharmSciTech, 2002, 4, E42). The kinetics of cell death depends on the number of stages and a set of parameters. $K_{max}$ represents the maximum cell kill rate, $KC_{50}$ represents a Michaelis constant, the drug concentration where half of the maximum rate is observed, tau ($\tau$) represents how fast cells progress through each stage, and $k_d$ represents the rate of natural cell death, that is, not resulting from the drugs.

FIG. 1b shows the design of the three-chamber μCCA, and a corresponding PK model of the device, and a PD model for each compartment. The complete equations used for the PK-PD model are listed hereinbelow.

Equations used for the PK-PD model:

5-FU in blood (reservoir):

$$V_B \cdot \frac{dC_{FU,B}}{dt} = Q_L \cdot C_{FU,L} + Q_T \cdot C_{FU,T} + Q_M \cdot C_{FU,M} - Q_B \cdot C_{FU,B}$$

5-FU in liver:

$$V_L \cdot \frac{dC_{FU,L}}{dt} = Q_L \cdot C_{FU,B} - Q_L \cdot C_{FU,L} - \frac{V_{m,FU} \cdot C_{FU,L} \cdot V_L}{K_{m,FU} \cdot \left(1 + \frac{C_{U,L}}{K_{i,U}}\right) + C_{FU,L}}$$

5-FU in tumor:

$$V_T \cdot \frac{dC_{FU,T}}{dt} = Q_T \cdot C_{FU,B} - Q_T \cdot C_{FU,T}$$

5-FU in marrow:

$$V_M \cdot \frac{dC_{FU,M}}{dt} = Q_M \cdot C_{FU,B} - Q_M \cdot C_{FU,M}$$

Uracil in blood (reservoir):

$$V_B \cdot \frac{dC_{U,B}}{dt} = Q_L \cdot C_{U,L} + Q_T \cdot C_{U,T} + Q_M \cdot C_{U,M} - Q_B \cdot C_{U,B}$$

Uracil in liver:

$$V_L \cdot \frac{dC_{U,L}}{dt} = Q_L \cdot C_{U,B} - Q_L \cdot C_{U,L} - \frac{V_{m,U} \cdot C_{U,L} \cdot V_L}{K_{m,U} \cdot \left(1 + \frac{C_{U,L}}{K_{L,FU}}\right) + C_{U,L}}$$

Uracil in tumor:

$$V_T \cdot \frac{dC_{U,T}}{dt} = Q_T \cdot C_{U,B} - Q_T \cdot C_{U,T}$$

Uracil in marrow:

$$V_M \cdot \frac{dC_{U,M}}{dt} = Q_M \cdot C_{U,B} - Q_M \cdot C_{U,M}$$

Abbreviations: FU: 5-Fluorouracil (5-FU); U: uracil; B: blood; L: liver; T: tumor; M: marrow; $C_{a,b}$: concentration of a in compartment b; $V_a$: Volume of compartment a; $Q_a$: Flow rate into compartment a.

Equations used for the PD model:

$$\frac{dC1}{dt} = k_g \cdot C1 \cdot \left(1 - \frac{C1}{C_{SS}}\right) - C4 \cdot C1 - k_d \cdot C1$$

$$\frac{dC2}{dt} = \frac{\frac{K_{max} \cdot FU}{KC_{50} + FU} - C2}{tau}$$

$$\frac{dC3}{dt} = \frac{C2 - C3}{tau}$$

$$\frac{dC4}{dt} = \frac{C3 - C4}{tau}$$

Abbreviations: $C_n$: Number of cells in the $n_{th}$ transit compartment; $K_{max}$: Maximum rate of cell death progression; $KC_{50}$: Saturation constant; FU: 5-Fluorouracil (5-FU); tau: Time constant for cell death progression; $k_d$: Natural cell death rate; $C_{SS}$: Maximum cell number that can be reached; $K_g$: Cell proliferation rate.

All the above equations for the PK-PD and PD models were solved using the ode45 routine of MATLAB® software, a high-level language and interactive environment with built-in math functions for numerical computation, visualization, and programming (Mathworks, Natick, Mass.). The parameters for the PD model were fitted to experimental data by using the lsqnonlin (non-linear least square) routine of the optimization toolbox in the MATLAB® software. The least square method finds the optimized parameters by minimizing the sum of squares of residuals (D. A. H. Jacobs and Institute of Mathematics and Its Applications, The state of the art in numerical analysis: proceedings of the Conference on the State of the Art in Numerical Analysis held at the University of York, Apr. 12-15, 1976, Academic Press, London, New York, 1977). The fitted parameters were $K_{max}$, $KC_{50}$, and kd (Tables 2 and 3). Other parameters were fixed at $C_0$=3000, $C_{ss}$=14 000, kg=0.001, $\tau$=5 (J. H. Sung, A. Dhiman and M. L. Shuler, J. Pharm. Sci., 2009, 98, 1885-1904). The viability at each time point was calculated as the ratio of the number of live cells to the number of total cells.

TABLE 2

Fitted parameter values for a PD model in static conditions

|  | HepG2/C3A | HCT-116 | Kasumi-1 |
| --- | --- | --- | --- |
| $K_{max}$/mM | 0.058 | 0.097 | 0.10 |
| $KC_{50}$ (l/day) | 5520 | 8610 | 7410 |
| $k_d$ (l/day) | 0.003 | 0.0029 | 0.0038 |

TABLE 3

Fitted parameter values for a PD model in dynamic conditions (μCCA)

|  | HepG2/C3A | HCT-116 | Kasumi-1 |
|---|---|---|---|
| $K_{max}$/mM | 0.047 | 0.031 | 0.03 |
| $KC_{50}$ (1/day) | 1670 | 205 | 247 |
| $k_d$ (1/day) | 0.0027 | 0.0002 | 0.0055 |

Incorporation of Hydrogel Cell Culture and Assembly of a μCCA

The device assembly process begins by placing the silicone gasket and the polycarbonate base on top of the aluminum frame (FIG. 1d). Then the cell culture chamber layer was placed on top. To prevent wrinkling of a 0.25 mm thin cell culture chamber layer, a drop of 95% ethanol was placed on top of the polycarbonate base before placing the chamber layer, and was evaporated in a hot oven. The assembled aluminum bottom frame, silicone gasket, polycarbonate base, and the cell culture chamber layer were sterilized by autoclaving. Cells were prepared and resuspended in 2% (w/v) alginate solution at $4 \times 10^6$ cells/ml. The alginate solution was made by dissolving alginate powder (10/60 LF sodium alginate, FMC biopolymer) in a HEPES buffer (15 mM HEPES, 92 mM sodium chloride), and filter sterilizing with 0.2 μm pore size syringe filter (VWR scientific, West Chester, Pa.). Cell-alginate suspensions of three cell types were prepared (HepG2/C3A, HCT-116, Kasumi-1), and 10 μl of each cell suspension was placed in corresponding cell culture chamber. A porous polycarbonate membrane filter (8 μm pore size, VWR Scientific, West Chester, Pa.) was placed on top to flatten the alginate, and sterile filtered 30 mM calcium chloride solution was applied onto each chamber to polymerize the hydrogel.

After 30 minutes of incubation at room temperature, calcium chloride solution and the membrane filter were removed. Then the top surface was flooded with 1 ml of DPBS, and the fluidic channel layer was placed on top, with channels facing down.

Sealing the Multi-Layered μCCA

To verify the sealing of the device in the presence of the hydrogel, fluorescent beads were encapsulated in 2% alginate and inserted into the device. This was an optional step to verify the sealing of the embodiment tested in this example. After device assembly, fluorescein solution was inserted into the device to visualize the channels, and the interface between the channels and hydrogel.

FIG. 11a shows a bright-field photomicrograph of an assembled embodiment of the μCCA. A cell culture chamber and channels are shown on the left side of the picture. FIG. 11b shows a fluorescein solution inserted to visualized the channel and test sealing. Channels are shown as horizontal stripes across the photomicrograph. Fluorescein also diffuses into alginate, staining it light green (light gray in the photomicrograph). FIG. 11c shows a cell culture chamber visualized with red fluorescent beads (appearing as bright spots in the photomicrograph), which were mixed with alginate and inserted into a μCCA.

Cell Viability After Long-Term Culture in a μCCA

To verify the long-term operation of a μCCA, cells were cultured in the device for five days with a daily medium replenishment. Cells maintained high viability for five days, verifying that the nutrient depletion and waste accumulation in the cell culture medium is the main cause of cell death in case the medium was not replenished.

FIGS. 12a-b show the live/dead staining result of cells cultured in a μCCA for five days with daily medium change.

6.1.3 Results

Device Assembly and Gravity-Induced Flow

Bonding of PDMS to glass by oxygen plasma treatment is the most common method of sealing a microfluidic device made of PDMS. However, a μCCA requires seeding multiple types of cells in a single device to mimic multi-organ interactions; therefore, the device was assembled after seeding each cell type into the chambers of the device. Although this method may not be as robust as the irreversible sealing by plasma bonding, the sealing was sufficiently complete to prevent the leakage of recirculating medium from the device during the 3-day operation. FIG. 1c shows the assembled device with color dye for visualization. The sealing at the interface between the channel and the cell culture chamber layer was verified by using a fluorescein solution and fluorescent beads (FIGS. 11a-c). The recirculation of cell culture medium was achieved by gravity-induced flow (FIG. 2a). The flow rate through the fluidic channels can be expressed by the following equation:

$$Q = \frac{\rho g \pi}{8 \eta} \frac{\Delta h R^4}{L} \qquad (2)$$

where Q is the volumetric flow rate (m³ s⁻¹), ρ is a density (kg m⁻³), g is the gravity constant (m s⁻²), η is a fluid viscosity (Pa s), Δh is a height difference (m), R is the radius of a channel (m), and L is the length of a channel (m). The μCCA device consists of several channels connected in parallel, and can be thought as a single hypothetical single channel when combined together. Also the equation assumes a circular channel, and the combined channels can be analyzed using an equivalent hydraulic diameter. Equation (1) indicates that the flow rate is linearly proportional to the height difference, and the experimental result shown in FIG. 2b demonstrates that this is true. However, the line does not extrapolate to zero intercept, as predicted by the equation. Such an observation is probably due to the finite size of the reservoir. The height difference (Δh) is measured as the distance from the top of the liquid in a higher well to the top of the liquid in a lower well. After the flow is initiated, Δh changes continuously as the liquid moves from the higher well to the lower well. This causes the system to deviate from the equation, and this would be more critical at a lower flow rate, that is, a smaller initial height difference (Δh).

Using the recirculation by gravity-induced flow, it was possible to operate the device for at least three days with cells maintaining good viability. FIGS. 6a-c shows the live/dead staining result for the three cell types cultured in the device for three days. After three days, cells appeared healthy, although different viability was observed depending on the cell type. For example, colon cancer cell line (HCT-116) showed viability close to 100%, whereas myeloblast (Kasumi-1) and hepatoma cell line (HepG2/C3A) showed lower viabilities. This difference demonstrates the variations in the cell response to the 3-D microfluidic environment. The observed trend in the cell viability agrees with the viability measured using Trypan-blue exclusion assay, as is discussed below. In addition, it should be noted that the result is for the case where the cell culture medium was recirculated without replenishment. Therefore, eventually nutrient depletion and/or waste accumulation in the recirculating medium would cause loss of cell viability. In case where the cell culture medium was replenished every day, cells maintained a higher viability for a longer period of time (FIGS. 13a-d).

Construction of a PK-PD model

A PD model for static hydrogel-cell cultures was constructed first. In the case of a static cell culture, a PK model is not needed, since no multi-organ interaction is expected to occur with a single cell type. A transit compartment model was constructed for each cell type, and the parameters for each cell type were fitted to experimental data. FIGS. 7a-c shows the experimental and the simulation results of the PD model in static conditions. The results show a slight variation in the responses of different cell types. For example, HepG2/C3A cells showed a slower drop in the viability than other cell types. Overall, simulated cell viabilities for the three cell types showed a good agreement with the experimental data, but PD models predicted more linear responses than the experimental results. This could imply that an additional molecular mechanism might be present, which is not fully described by the transit compartment model.

A PK model for the μCCA was constructed with three different 5-FU concentrations. FIG. 8a shows the predicted concentration profiles of 5-FU in the device for the three dosing conditions. Due to the combination of uracil with 5-FU, metabolism of 5-FU was inhibited, and almost constant concentrations of 5-FU were maintained for 72 h. The short residence times in each compartment (100, 240, 180 s for the liver, tumor and the marrow compartment) ensured that all compartments were quickly equilibrated with medium reservoir. Once the PK model was constructed, the 5-FU concentration profile in each compartment was used as an input for a PD model in the same compartment. The parameters for the PD models were fitted to the cell viability result of the corresponding cell type, which are summarized in Tables 2 and 3.

FIGS. 8b, c, and d show the measured and simulated viabilities of the liver, tumor and myeloblasts cell lines, respectively. Interestingly, a large variation in the cell responses was observed, depending on the cell type. In addition, cell responses in dynamic conditions (μCCA) were drastically different from those of static conditions. In general, cells were more sensitive to 5-FU in dynamic conditions than static conditions. Also, the differences between the cell types were more distinct in a μCCA than in static conditions. For example, tumor (HCT-116) and myeloblasts (Kasumi-1) cell lines were much more sensitive to 5-FU treatment than hepatoma (HepG2/C3A) cell line. The behavior of the cells in the absence of drugs were markedly different, too. For example, the viability of myeloblasts was about 60% on day 3. The tumor cell line maintained a high viability throughout the three-day period. On the other hand, in static conditions, the cell behaviors in the absence of drugs were similar to one another, and all cells showed a gradual decrease in cell viability over three days.

Effect of Uracil as a Modulator

5-FU is known to be metabolized mainly through the enzyme dihydropyrimidine dehydrogenase (DPD) (A. B. Van Kuilenburg, R. Meinsma, L. Zoetekouw and A. H. Van Gennip, Int. J. Cancer, 2002, 101, 253-258). About 80% of administered 5-FU is thought to be metabolized by DPD (G. D. Heggie, J. P. Sommadossi, D. S. Cross, W. J. Huster and R. B. Diasio, Cancer Res., 1987, 47, 2203-2206). Uracil inhibits 5-FU metabolism by competitive inhibition, enhancing the action of 5-FU (J. S. de Bono and C. J. Twelves, Invest. New Drugs, 2001, 19, 41-59). The effect of uracil as a modulator of 5-FU toxicity was tested by comparing the responses of cells to 5-FU plus uracil and 5-FU alone. First, cells were encapsulated in alginate in a μCCA and the responses were compared (FIG. 9a). In this case, the difference in the cell viability between 5-FU alone and 5-FU plus uracil was not significant. Cells were also encapsulated in a different hydrogel, MATRI-GEL®, in a μCCA. In this case, combination of uracil with 5-FU showed an enhanced cytotoxic effect compared to 5-FU alone, especially in the case of tumor and myeloblast cell lines (FIG. 9b).

Alginate and MATRIGEL® have different chemical compositions and mechanical properties, which may alter the attachment and physiology of encapsulated cells. A different encapsulating hydrogel may possibly result in a different metabolic activity of live cells. This hypothesis was tested by a mathematical simulation, where the PK and PD profiles for the two dosing conditions were compared with either normal or three-fold lower metabolic activities (FIGS. 10a-d). In case of normal metabolic activity, the absence of uracil is predicted to cause faster metabolism of 5-FU, resulting in about 80% reduction in 5-FU concentration on day 3 compared to 5-FU plus uracil. Consequently, cell viabilities are predicted to be higher when treated with 5-FU only, than 5-FU plus uracil.

In the second case, the value of $V_{max}$ in the PK-PD model was reduced threefold. In this case, metabolism of 5-FU is much slower, and the presence or absence of uracil does not have as much effect on the pharmacokinetics of 5-FU. Consequently, the predicted cell viabilities in both cases are similar.

6.1.4 Discussion

Advantages of Layered Design

One of the aims of the work described in this example was to develop a 'user-friendly' microfluidic device, with relatively easy device assembly and operation, potential high-throughput implementation, and data extraction. These conditions had to be met while still enabling culturing multiple cell types in separate chambers in a single device. Oxygen plasma treatment, which is the most common method of sealing a PDMS device, would damage the cells. Equipping the microfluidic device with a fluidic-control system such as pneumatic valves would allow sealing the device before cell seeding (M. A. Unger, H. P. Chou, T. Thorsen, A. Scherer and S. R. Quake, Science, 2000, 288, 113-116), but this approach would increase the complexity of the device, which contradicts our initial objective. The separate PDMS layers allowed the seeding of multiple cell types simultaneously, and reversible sealing allows retrieval of cells from the device during or after a run of the device for further analysis.

Using gravity offers several advantages over using a pump. First, removal of an external pump reduces the total space occupied by the device and enables a more high-throughput implementation at a lower cost. Secondly, use of silicone tubing may cause adsorption of molecules on the inner surface, and gravity-induced flow eliminates the possibility of unwanted binding. Thirdly, using gravity solves the problem of air bubble formation, since air bubbles are prevented from entering the device due to their buoyancy. The formation of air bubbles is a notorious problem in microfluidic systems, and several attempts have been made to avoid this by using an external or in-line bubble trap (J. H. Kang, Y. C. Kim and J. K. Park, Lab Chip, 2008, 8, 176-178; A. M. Skelley and J. Voldman, Lab Chip, 2008, 8, 1733-1737; J. H. Sung and M. L. Shuler, Biomed. Microdevices, 2009, 11, 731-738). However, the performance of a bubble trap is not always perfect, and it has a limit in its bubble-trapping capacity. Overall, the usability of the μCCA was greatly enhanced with the new design, compared to the previous version (K. Viravaidya, A. Sin and M. L. Shuler, Biotechnol. Prog., 2004, 20, 316-323).

It should be noted that the use of gravity-induced flow and a rocking platform results in a reciprocating mode of recirculation; instead of a continuous, closed-loop recirculation, the direction of the flow changes every time the rocking platform changes its angle. The potential effect of the reciprocating recirculation on the pharmacokinetic profiles of drugs was tested (FIGS. 13a-d). It was verified by a mathematical simulation that reciprocating recirculation causes a negligible deviation on the PK of a prodrug and a metabolite from those values predicted for continuous, closed-loop recirculation.

Insights from a PK-PD model of a KCA

An integrated PK-PD model for a μCCA was developed by constructing a PBPK model and a PD model separately, and combining the two. The growth of cells encapsulated in alginate was assumed to be negligible, because no significant cell growth was observed during the three-day period when encapsulated in alginate matrix. This observation was consistent with previous studies by other researchers, where cell growth was poor in alginate due to the human cell's inability to attach to negatively charged polymers (M. A. Lawson, J. E. Barralet, L. Wang, R. M. Shelton and J. T. Triffitt, Tissue Eng., 2004, 10, 1480-1491). However, alginate can be chemically modified with peptides that can alter cell attachment and physiology (J. Yu, Y. Gu, K. T. Du, S. Mihardja, R. E. Sievers and R. J. Lee, Biomaterials, 2009, 30, 751-756). Comparison of optimized parameters gave a further insight into the behavior of cells in various conditions.

In the transit compartment model, $K_{max}$ shows how quickly cells progress through the cell death mechanisms, and $KC_{50}$ shows the concentration range of the drug in which they are most sensitive. A brief comparison of cell death kinetics in FIGS. 7a-c and 8a-d show that in dynamic conditions (μCCA), cells go through cell death more rapidly. A quantitative comparison of the parameters in Tables 2 and 3 demonstrates that the differential response is caused by lower values of $KC_{50}$ in dynamic conditions. This suggests that in dynamic conditions, cells were more sensitive in a lower concentration range than in static conditions.

In addition, differential behaviors between cell types could also be observed. In both static and dynamic conditions, the liver cells (HepG2/C3A) were most resistant to 5-FU than other two cell types, demonstrated by a lower value of $K_{max}$ or a higher value of $KC_{50}$. This observation is consistent with previous clinical findings that hematological toxicity was the dose-limiting toxicity of 5-FU (D. Testart-Paillet, P. Girard, B. You, G. Freyer, C. Pobel and B. Tranchand, Crit. Rev. Oncol. Hematol., 2007, 63, 1-11; A. B. van Kuilenburg, Eur. J. Cancer, 2004, 40, 939-950). The value of $k_d$ reveals the 'natural' death rate, that is, cell death when drugs are not present. In static conditions, the values of $k_d$ were similar in all three cell types, whereas in a μCCA, the values varied widely between the cell types, implying that cells have differential adaptability to the microfluidic environment.

This dependency of cell responses on cell types and culture environment demonstrates the fact that conventional in vitro cell based assays may not necessarily reflect the drug effects that would be observed in the same environment under dynamic conditions. It is especially interesting to note that the differences between cell types were greater in microfluidic environment. It is not clear why the cells in dynamic conditions respond differently from the cells in static conditions. However, it has been observed by several researchers that the presence of flow often has a significant effect on the physiology and the behavior of cells (N. A. Mufti and M. L. Shuler, Biotechnol. Prog., 1995, 11, 659-663; C. R. White and J. A. Frangos, Philos. Trans. R. Soc. London, Ser. B, 2007, 362, 1459-1467; N. M. Matharu, G. E. Rainger, R. Vohra and G. B. Nash, Biorheology, 2006, 43, 31-44). In addition to the effect of flow, presence of multiple cell types in a single device, even without a direct, physical contact, could affect the cell functions (F. Vozzi, J. M. Heinrich, A. Bader and A. D. Ahluwalia, Tissue Eng., Part A, 2009, 15, 1291-1299). The combination of these factors may have contributed to the different responses of the cells in the static and dynamic conditions.

FIGS. 10a-d show the predicted pharmacokinetic profile of 5-FU under two conditions, one with a normal rate of 5-FU metabolism, and one with a low rate of 5-FU metabolism. In all cases, combination of uracil resulted in a higher concentration of 5-FU than the administration of 5-FU alone, but the difference was significantly smaller with a lower metabolism rate. Consequently, combination of uracil enhanced the efficacy of 5-FU, only when the metabolism rate of 5-FU was normal. Also, the difference in the resulting cell viabilities on day 3 is much smaller than the difference in the predicted 5-FU concentrations. This is because the mechanism of cell death due to a chemotherapeutic agent is time-dependent, and often the response of tumor cells is observed in a time-delayed manner (E. D. Lobo and J. P. Balthasar, AAPS PharmSciTech, 2002, 4, E42). This is consistent with experimental observation in FIG. 9b. A longer experiment than three days will yield a greater difference in the cell viabilities. Cells remained healthy for 5 days when cell culture medium was replenished daily, but for the drug experiment, cell medium could not be replaced because metabolites have to be retained. This eventually causes nutrient depletion, waste accumulation, and possibly a change in osmolarity due to evaporation, which would compromise cell survival.

Effect of Encapsulating Matrix on Cell Function

HepG2/C3A is a hepatoma-derived cell line, which is commonly used for assessing liver function. However, it is known to retain only minimal liver-metabolic activity (S. Wilkening, F. Stahl and A. Bader, Drug Metab. Dispos., 2003, 31, 1035-1042). Furthermore, it is possible that culturing cells in alginate matrix would alter the metabolic function of the cells, since alginate polymers with negative charges prevent cell attachment, and do not provide functional groups necessary for proper cell signaling and function (M. A. Lawson, J. E. Barralet, L. Wang, R. M. Shelton and J. T. Triffitt, Tissue Eng., 2004, 10, 1480-1491). It has been reported that the hepatic function of cultured hepatocytes can be enhanced by culturing them in a more naturally derived hydrogel such as collagen or MATRIGEL® (J. V. Castell and M. J. Gomez-Lechon, Methods Mol. Biol., 2009, 481, 35-46; E. F. Brandon, C. D. Raap, I. Meijerman, J. H. Beijnen and J. H. Schellens, Toxicol. Appl. Pharmacol., 2003, 189, 233-246). In this example, a comparative study of encapsulating cells in alginate or MATRIGEL®, and treating them with 5-FU alone or 5-FU plus uracil indicated that the metabolism of 5-FU may be slower in alginate than in MATRIGEL®.

Comparison of Pharmacokinetic Profile of a Prodrug and Its Metabolite in Two Different Modes of Recirculation Utilization of a rocking platform and gravity-induced flow results in a different recirculation pattern from the recirculation using a peristaltic pump. The direction of the flow changes every three minutes, rather than forming a continuous, closed-loop recirculation. The pharmacokinetic profiles of a hypothetical prodrug (A), and its metabolite (B) were simulated with a mathematical model representing the two modes. Each compartment was segregated into five sub-compartments, since using well-mixed assumption for the compartment neglects any difference that may be caused the reciprocating recirculation. In the first model (FIG. 13a), a continuous recirculation is shown, where the flow coming out of each compartment goes back into the reservoir for recirculation. In case of gravity-induced flow, the direction of the flow changes every time the rocking platform changes its angle, which is about every three minutes (FIG. 13b). A mathematical model describing each situation was constructed, and a conversion of A into B was simulated using same parameters (Table 4).

TABLE 4

Parameters for the PK model

| Name | Value | Unit |
|---|---|---|
| $V_{liver}$ | $11.3 \times 10^{-3}$ | ml |
| $V_{tumor}$ | $11.3 \times 10^{-3}$ | ml |
| $V_{marrow}$ | $11.3 \times 10^{-3}$ | ml |
| $V_{blood}$ | 1.5 | ml |
| $Q_{liver}$ | 87.6 | µl/min |
| $Q_{tumor}$ | 26.7 | µl/min |
| $Q_{marrow}$ | 35.6 | µl/min |
| $Q_{blood}$ | 149.9 | µl/min |
| $V_{m1}$ | 80 | nmol/min |
| $K_{m1}$ | 2700 | nmol/ml |
| $V_{m2}$ | 0.5 | nmol/min |
| $K_{m2}$ | 40 | nmol/ml |

In both cases, the rate of depletion of A and synthesis of B were almost identical. Additionally, the rocking platform continuously changes its angle during the three minutes, thus effectively changing the flow rate, until it changes the direction of the flow. However, this aspect was neglected in the model, and the constant flow rate was assumed during each three-minute period.

6.1.5 Conclusion

A microfluidic device based on a mathematical PK-PD model was developed. The layer-by-layer design and the use of gravity induced flow allowed relatively easy assembly and operation of the device for several days by eliminating the need for an external pump, and preventing bubble formation inside microfluidic channels. A mathematical model describing the pharmacokinetics (PK) and pharmacodynamics (PD) of 5-FU in the device was constructed, and fitted to the experimental results from a µCCA. Optimization of parameters for the model provided an insight into the differential responses of cells to the drug in various environments. Combination of PK-PD modeling and a µCCA can provide a novel in vitro/in silico platform for testing the effect of drugs in a PK-PD based manner.

6.2 Example 2

Embodiment of Microfluidic Device for Pharmacokinetic-Pharmacodynamic (PK-PD) Study of Drugs 6.2.1 Background One of the fundamental challenges that a pharmaceutical industry faces during drug development process is extrapolation of in vitro cell-based assay to human response. Currently, the most common form of in vitro cell-based assay is multiwell plate assay, such as 96 or 384 well plates. These assays, however, often give results that are different from human responses, which increases the probability of the drug failing in clinical trials and increasing the cost of development. The main reasons for inaccurate predictions by such multiwell plate assays are 1) only single cells types are generally tested in a single well, which does not provide complex multi-organ interactions in the human body. 2) cells are cultured in 2-D monolayer cell culture inside the wells, and the behavior of cells cultured in 2-D monolayer is vastly different from the behavior of cells in their native tissue, where they are surrounded by various extracellular matrix and neighboring cells in 3-D environment. The use of microfluidics has been introduced as a way of increasing the efficiency of cell-based tests. Although current microfluidic devices can increase the efficiency of high-throughput screening by automated fluid introduction through microfluidic channels and valves, it is essentially the same concept as the multiwell plate based assay system regarding that a single cell type is tested in a physiologically non-relevant environment, and therefore share the same limitations of multiwell plate system that were mentioned above.

The issue which is difficult to overcome using these devices is the authenticity of the cells cultured in the device. Cells do not behave the same way as they do in their native environment when they are removed from body and cultured in 2-D monolayer. Often cells exhibit more authentic behavior when they are cultured in 3-D environment, such as hydrogel matrix. Liver cells (hepatocytes) have been shown to exhibit high liver-specific functions when they are cultured in collagen-sandwich culture (LeCluyse et al, *Pharm Biotechnol*, 8, 121-59, 1996), encapsulated by alginate matrix or when they form spheroids (Khalil et al, *J. Hepatol*, 297, 68-77, 2001). Tumor cells have shown different responses to the same chemotherapeutic agent when they are cultured in 3-D hydrogel matrix and when they are cultured in 2-D monolayer (Walker et al, *Toxicol In Vitro*, 14, 5, 475-85, 2000), implying current methodologies employed by pharmaceutical industry may not be an optimal method to evaluate drug candidates.

In addition to culturing cells in 3-D environment, it has been found that having a precise control on the transport of nutrients and oxygen is important in eliciting authentic cell functions in vitro. When cultured in vitro, cells are maintained in a homogeneous environment where oxygen and nutrients are supplied at sufficiently high level. For example, when cells are cultured in a cell culture dish, cells are immersed in cell culture medium, where cells are exposed to the same condition regardless of their location. Medium is changed periodically to ensure high levels of nutrients and the medium height is adjusted to allow sufficient oxygen transport through diffusion. In native tissue, cells reside in heterogeneous environment, where they are exposed to different conditions from one another, depending on their locations and their functions. Hepatocytes in the liver perform various tasks of metabolism and detoxifications, and their functions are regulated by local oxygen concentration. For example, hepatocytes located in periportal zone are exposed to high oxygen tension and mainly perform glucose, albumin synthesis and detoxification by glutathione conjugation, whereas in perivenous zone with low oxygen tension their main function is the synthesis of antitrypsin and detoxification by glucuronidation and oxidation by cytochrome P450 enzymes. This implies that just providing hepatocytes with excess nutrients and oxygen is not necessarily an optimal strategy to induce their liver-specific functions in vitro.

Similarly, malignant cells in a tumor tissue are often exposed to a low oxygen tension and in response to their environmental cues express various growth and angiogenic factors for their survival. Simply culturing tumor cells in a dish with sufficient oxygen supply may not necessarily reproduce the real environment they are exposed to, and may alter the cell responses. In an approach to reproduce the physiological environment of hepatocytes, microfluidic devices have been used for seeding cells in a matrix. However, these devices do not allow culture of multiple cell types to reproduce multi-organ interactions, and therefore is an incomplete system for testing the effect of drugs on target cells. In addition, silicon matrices used in other devices do not provide a physiologically realistic substrate for cell culture, compared to hydrogels such as alginate or MATRIGEL®.

6.2.2 Fabrication of an Embodiment of the Microfluidic Device

Fabrication of Channel Layer

The channel layer is fabricated from PDMS using soft-lithography techniques. The patterns of channels are drawn using AutoCAD, and which are transferred to a chrome mask and developed. A master is made by spin-coating SU-8 on a silicon wafer and exposing/developing the pattern on the mask. PDMS is poured onto the master and cured to make the channel patterns, which are cut into 25 mm by 25 mm pieces.

Fabrication of the Cell Culture Chamber (Gel) Layer

The cell culture chamber layer is made from silicone sheet of defined thickness (from 100 micrometer to over 1 mm) Holes are punched in the sheet using a biopsy punch of desired size (from 2 mm to 8 mm diameter) at the appropriate locations, aligned with the locations of channels.

Polycarbonate Base

A polycarbonate base provides a solid support for the hydrogel-cell mixture and fabricated from a 1 mm thick polycarbonate piece (25 mm by 25 mm) by drilling 0.5 mm diameter holes aligned with inlet and outlet holes in the aluminum bottom frame Silicone Gasket A silicone gasket provides a seal between the aluminum bottom frame and the polycarbonate base. It is made from 2 mm thick silicone sheet with 4 mm holes punched in alignment with inlet and outlet holes in the aluminum bottom frame.

Aluminum Bottom Frame and PLEXIGLAS® Top Frame

Bottom and top frames provide the housing for the whole device, with four holes for screws to secure and seal the device. A top frame is machined from 30 mm by 30 mm PLEXIGLAS®, to enable visual inspection, and four holes are drilled on each side. Bottom frame is machined from aluminum to enable sterilization by autoclaving, and consists for four holes for screws on each side and inlet and outlet holes for medium perfusion.

Cell Seeding in Hydrogel and Assembly of the Device

The first cell type is collected and suspended in appropriate solution of sodium alginate (0.5%~4%), which has been filter sterilized. The alginate-cell mixture is pipetted into the first chamber in the cell culture chamber layer. The volume of the alginate-cell mixture to be placed into the chamber is determined by the thickness of the cell culture chamber layer and the area of the chamber. The process of collecting the cells and placing the alginate-cell mixture into the chambers is repeated for each cell type and chamber that needs to be placed inside the device. After all the chambers have been filled, sterile polycarbonate membrane with 8 micrometer pore size is gently placed on top of the cell culture chamber layer. 30 mM calcium chloride solution is then pipetted onto the holes, so that the calcium chloride solution diffuses through the polycarbonate membrane into the alginate-cell mixture. After incubation at room temperature for 20 minutes, polycarbonate membrane is removed, and PBS is placed on top of the cell culture chamber layer to remove any air bubbles. A channel layer is then closed on top of the cell culture chamber layer in a tilted manner to push out air. The top PLEXIGLAS® frame is closed and secured with screws.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A microfluidic device for culturing cells and/or tissue comprising:
   a base layer;
   a cell culture chamber layer comprising one or more cell culture chambers;
   a fluidic channel layer comprising a plurality of fluid channels;
   a bottom frame;
   a gasket; and
   a top frame,
   wherein:
   the cell culture chamber layer is positioned between the fluidic channel layer and the base layer so that the one or more cell culture chambers are fluidically connected to one or more fluid channels of the plurality,
   the fluid channels have defined geometries that produce one or more desired flow rates through the fluid channels that simulate one or more physiological environments or conditions of interest,
   the bottom frame has an inlet hole and an outlet hole,
   the base layer has an inlet hole and an outlet hole, and
   the cell culture chamber layer has an inlet hole and an outlet hole, and
   wherein the inlet holes of the bottom frame, the base layer and the cell culture chamber layer and the outlet holes of the bottom frame, the base layer and the cell culture chamber layer align with one another, thereby allowing circulation of fluid through the cell culture chamber layer and the fluidic channel layer.

2. The microfluidic device of claim 1, wherein the physiological environment or condition of interest is blood flow distribution to an organ or tissue of interest.

3. The microfluidic device of claim 1, wherein the gasket is positioned on an interior surface of the bottom frame between the bottom frame and the base layer.

4. The microfluidic device of claim 1, wherein the cells comprise a single cell type or a plurality of cell types.

5. The microfluidic device of claim 4 wherein a single cell type of the plurality is cultured in a single cell culture chamber.

6. The microfluidic device of claim 4 wherein two or more cell types of the plurality are cultured in a single cell culture chamber.

7. The microfluidic device of claim 1, wherein the cells or tissue are cultured in or on a 2-D matrix, a 3-D matrix or a scaffold.

8. The microfluidic device of claim 1, wherein the cells or tissue are encapsulated.

9. The microfluidic device of claim 1, wherein a fluid flow pattern is induced by gravity, static flow or pump perfusion.

10. The microfluidic device of claim 9 wherein the gravity induced fluid flow pattern is induced by reciprocating motion.

11. The microfluidic device of claim 9 comprising a pair of reservoirs, wherein the reciprocating fluid motion is between the pair of reservoirs.

12. The microfluidic device of claim 9 wherein the gravity induced fluid flow pattern simulates blood circulation through a tissue or organ of interest.

13. The microfluidic device of claim 1, that can be reversibly assembled and disassembled.

14. A method for culturing cells or tissues comprising the steps of:
providing the microfluidic device of claim 1;
placing the cells or tissues to be cultured in the microfluidic device; and
culturing the cells or tissues,
wherein the culturing step comprises flowing cell or tissue culture medium through the microfluidic device.

15. The method of claim 14 comprising the step of encapsulating cells to be cultured in a hydrogel.

16. The method of claim 14 wherein the cells or tissues are cultured in or on a 2-D matrix, a 3-D matrix or a scaffold.

17. The method of claim 14 wherein the step of flowing cell or tissue culture medium is induced by gravity, static flow or pump perfusion.

18. The method of claim 14 comprising the step of performing an analysis or assay of an effect of an agent of interest on the cultured cells or tissue, thereby determining an in vitro effect of the agent of interest on the cultured cells or tissue.

19. The method of claim 18 wherein the in vitro value of the effect is comparable to the in vivo value of the effect for a cell or tissue type of interest.

20. The method of claim 14 comprising the step of performing a pharmacokinetic, a pharmacodynamic or a pharmacokinetic-pharmacodynamic (PK-PD) assay or analysis of an effect of an agent of interest on the cultured cells or tissue, thereby determining an in vitro pharmacokinetic and/or pharmacodynamic effect of the agent of interest on the cultured cells or tissue.

21. The method of claim 20 wherein the in vitro pharmacokinetic or pharmacodynamic value is comparable to the in vivo pharmacokinetic or pharmacodynamic value for a cell or tissue type of interest.

22. The method of claim 14 wherein a plurality of microfluidic devices are provided, further comprising the step of conducting a high throughput analysis.

23. The method of claim 14 wherein a plurality of cell types are cultured, further comprising the step of testing the effect of an agent of interest on the plurality of cell types.

24. The method of claim 23 wherein the effect of an agent of interest and its metabolite(s) are tested simultaneously.

25. A method for culturing cells for tissue engineering comprising the steps of:
providing the microfluidic device of claim 1;
placing the cells to be cultured in the microfluidic device; and
culturing the cells, wherein the culturing step comprises flowing cell culture medium through the microfluidic device; and
harvesting the cultured cells.

26. The method of claim 25 comprising the step of encapsulating cells to be cultured in a hydrogel.

27. The method of claim 25 wherein the cells or tissues are cultured in or on a 2-D matrix, a 3-D matrix or a scaffold.

28. The method of claim 25 wherein the step of flowing cell culture medium is induced by gravity, static flow or pump perfusion.

29. A method for performing a pharmacokinetic, a pharmacodynamic or a pharmacokinetic-pharmacodynamic (PK-PD) assay of an effect of an agent of interest on cultured cells or tissues of interest comprising the steps of:
providing the microfluidic device of claim 1;
culturing the cells or tissues in the microfluidic device;
exposing the cultured cells or tissues to the agent of interest; and
determining an in vitro pharmacokinetic and/or pharmacodynamic effect of the agent of interest on the cultured cells or tissue.

30. The microfluidic device of claim 1, wherein cells or tissue are grown in one or more fluid channels of the plurality of fluid channels.

31. The microfluidic device of claim 1, wherein prior to assembly of the microfluidic device, cell culture chambers in the cell culture chamber layer are not fluidically connected to the fluid channels in the fluidic channel layer.

* * * * *